(12) United States Patent
Seok

(10) Patent No.: US 11,717,624 B2
(45) Date of Patent: Aug. 8, 2023

(54) MODULARIZED VAPORIZER

(71) Applicant: LV-lab, Seoul (KR)

(72) Inventor: Insun Seok, Seoul (KR)

(73) Assignee: LV-lab, Seoul (KR)

( * ) Notice: Subject to any disclaimer, the term of this patent is extended or adjusted under 35 U.S.C. 154(b) by 997 days.

(21) Appl. No.: 16/248,428

(22) Filed: Jan. 15, 2019

(65) Prior Publication Data

US 2019/0142071 A1 May 16, 2019

Related U.S. Application Data

(63) Continuation-in-part of application No. PCT/KR2017/007570, filed on Jul. 14, 2017.

(30) Foreign Application Priority Data

Jul. 16, 2016 (KR) .................. 10-2016-0090339

(51) Int. Cl.
*A24F 47/00* (2020.01)
*A61M 15/06* (2006.01)
*A24F 40/46* (2020.01)
*A24F 40/48* (2020.01)
*A24F 40/485* (2020.01)
*A24F 40/42* (2020.01)
*A24B 15/167* (2020.01)
*F22B 3/02* (2006.01)
*A24F 40/50* (2020.01)

(52) U.S. Cl.
CPC .......... *A61M 15/06* (2013.01); *A24B 15/167* (2016.11); *A24F 40/42* (2020.01); *A24F 40/46* (2020.01); *A24F 40/48* (2020.01); *A24F 40/485* (2020.01); *F22B 3/02* (2013.01); *A24F 40/50* (2020.01)

(58) Field of Classification Search
CPC ........... A61M 15/16; F22B 3/02; A24F 40/40; A24F 40/42
See application file for complete search history.

(56) References Cited

U.S. PATENT DOCUMENTS

| | | | |
|---|---|---|---|
| 2013/0192618 A1* | 8/2013 | Li | A24F 40/44 131/329 |
| 2015/0027469 A1* | 1/2015 | Tucker | A24D 3/17 131/329 |
| 2015/0128971 A1* | 5/2015 | Verleur | H02J 7/0045 131/329 |
| 2015/0351456 A1* | 12/2015 | Johnson | A24F 40/30 131/329 |
| 2018/0070637 A1* | 3/2018 | Deng | A24F 40/485 |
| 2020/0008469 A1* | 1/2020 | Reevell | H05B 3/0014 |

* cited by examiner

*Primary Examiner* — Eric Yaary
(74) *Attorney, Agent, or Firm* — United One Law Group LLC; Kongsik Kim; Jhongwoo Peck

(57) ABSTRACT

The present invention relates to a modularized vaporizer, which enables a fuel module, a heating module, or a vaporizing module to be coupled and separated, in a drawer manner, to and from a body portion housing since a fuel module chamber, a heating module chamber, or a vaporizing module chamber is provided in the body portion housing. The modularized vaporizer reduces the carbonization of fuel or an absorbent member since the fuel or a surface of the absorbent member is uniformly heated (irradiation) by heating energy (light, beam, or heat) emitted (irradiation) from a heating member of the heating module.

12 Claims, 18 Drawing Sheets

Related Art

MODULARIZED VAPORIZER

CROSS-REFERENCE TO RELATED APPLICATIONS

This application is a Continuation in Part application of International Application No. PCT/KR2017/007570 filed on Jul. 14, 2017, which claims priority to Korean Patent Application No. KR 10-2016-0090339 filed on Jul. 16, 2016, which applications are incorporated herein by reference.

TECHNICAL FIELD

The present invention relates to a device that vaporizes fuel, and more particularly, to a vaporizer applied to an antismoking adjuvant, an electronic cigarette, a fumigation treatment device, and the like which vaporize a liquid (fuel) using a vaporization device using electrical energy generated by a battery.

RELATED ART

Vaporizers such as an antismoking adjuvant, an electronic cigarette, a fumigation treatment device, and the like have been developed and used for helping people with quitting smoking.

Such devices generally include a suction portion, a cartridge, and a battery portion. The cartridge includes a liquid accommodation space and a vaporizing device. In the vaporizing device, an absorbent member, which holds a liquid, comes into surface contact with the liquid accommodation space, a heating wire converting electrical energy of a battery into heat energy is wound on the absorbent member, and when power of the battery is applied, the heating wire generates heat energy to vaporize the liquid held by the absorbent member such that the vaporized gas is discharged through the suction portion.

FIGS. 1 and 2 illustrate a conventional vaporizing device. A configuration of the conventional vaporizing device has a structure in which a heating wire is wound on an absorbent member such as 101 in FIGS. 1 and 102 and 103 in FIG. 2. A material of the heating wire (heating member) generally includes a platinum wire, a nickel-chrome alloy, iron including rare-earth elements, chrome, or an aluminum alloy wire.

Electrical energy supplied by a battery is converted to heat energy by the heating wire (heating member), and the heating wire (heating member) vaporizes a liquid which comes into surface contact therewith. In order to bring the liquid into surface contact with the heating wire, a heat-resistant absorbent member (fiber glass, silica wick, mesh, cotton, hanji (Korean traditional paper), and the like) is used.

However, the above-described related art has problems that a carbide (harmful substance) is generated due to a direct contact part between a heating wire and an absorbent member or a part of a heating wire at a high temperature which does not come into surface-contact with a liquid but is exposed to the air, a risk is caused by an excessive amount of a particular component (particularly, an accident caused by an excessive amount of nicotine) being mixed when a liquid fuel is used, filling of fuel is inconvenient, a heating wire is wound on an absorbent member to transfer fuel to the heating wire to vaporize the fuel, and fuel is necessarily limited to a liquid type fuel.

SUMMARY

The present invention is directed to providing a modularized vaporizer. According to aspects of the present invention, generation of a carbide may be suppressed by uniformly emitting heating energy toward a particular surface of fuel (a liquid) while avoiding direct contact surfaces among a heating energy supply member, an absorbent member, and a liquid. A complicated power structure of a heating wire vaporizing device may be improved, and a failure caused by disconnection and inconvenience of manufacturing by winding the heating wire on the absorbent member, which are problems of a heating wire vaporization method, may be solved.

Further, an excessive amount of a particular component being mixed may be prevented, and inconvenience in filling may be eased by converting fuel into a quantified solid (including a solidified fuel) type fuel. A vaporizing device may be configured to be replaced from the outside more easily and simply. A liquid fuel may also be filled more conveniently, and an absorbent member, which needs regular replacement, may be simply replaced.

Aspects of the present invention provides a modularized vaporizer having one or more of the following features. First, instead of a conventional vaporizing method of winding a heating wire on an absorbent member, a vaporizing device may be configured to uniformly heat a heating energy receiving surface of fuel (or an absorbent member) using a light (beam) vaporization method using a laser, infrared rays, ultraviolet rays, a halogen lamp, and the like, or by fixing a heating wire to a particular surface.

Second, the fuel may be solidified into a quantified component and stored in a fuel module such that the fuel module is coupled with or separated from a fuel module chamber of a housing in a drawer manner.

Third, a heating module including a heating member may be coupled with or separated from a heating module chamber of the housing in a drawer manner.

Fourth, when a liquid fuel is used, a liquid fuel module may be coupled with or separated from a fuel module chamber of the housing in a drawer manner. An absorbent member module may be coupled with or separated from an absorbent member module chamber of the housing in a drawer manner. Alternatively, an absorbent member may be coupled with or separated from the liquid fuel module in a thread-coupling manner.

In an aspect of the present invention, the modularized vaporizer may include a suction portion and a body portion. The body portion may include a body portion housing; a fuel module that stores a fuel and includes an open surface to receive a light energy; a heating module coupled to the body portion housing and disposed apart from the fuel module, wherein the heating module includes a heating member that emits the light energy; a vaporization space disposed between the heating module and the fuel module, wherein a vapor is released into the vaporization space by the light energy emitted from the heating module toward the fuel module through the vaporization space; and an air current pipe which is a path for transferring the vapor released in the vaporization space to the suction portion.

In particular, the body portion housing may include at least one module chamber to accommodate the fuel module or the heating module, and each of the at least one module chamber may include a first open surface and a second open surface across the body portion housing. The fuel module or the heating module may be pushed into the first open surface of the module chamber to be coupled therewith, and may be pushed from the second open surface of the module chamber to be separated therefrom.

In another aspect of the present invention, the modularized vaporizer may include a suction portion and a body portion. The body portion may include a body portion housing; a vaporization module chamber formed within the body portion housing; a vaporization module coupled to the vaporization module chamber, wherein the vaporization module comprises a heating module having a heating member that emits a light energy; and an air current pipe that transfers vaporized fuel to the suction portion.

In particular, the vaporization module chamber may include a first open surface and a second open surface across the body portion housing to allow the vaporization module to be pushed into the first open surface of the vaporization module chamber and coupled therewith, and to be pushed from the second open surface of the vaporization module chamber to be separated therefrom.

According to the present invention, one of more of the following effects may be provided. A heating member, which is a heating energy supply member, may uniformly irradiate a particular surface of fuel (or an absorbent member) to suppress generation of a carbide (harmful substance). Since a power connection structure may be unnecessary for a fuel module which receives heating energy, inconveniences such as a failure caused by disconnection in manufacturing, winding a heating wire on an absorbent member, and the like may be prevented.

Since an excessive amount of a particular component being mixed is prevented using a quantified solid fuel, safety and reliability of a product may be improved. In addition, since a solid fuel is stored in a fuel module and the fuel module is configured to be coupled with or separated from a fuel module chamber of a housing in a drawer manner, the fuel may be more easily and conveniently filled.

Since a heating module is coupled with or separated from a heating module chamber of the housing, replacement thereof may be more easily and conveniently performed, and a heating module adequate for properties or intension of heating energy may be applied as necessary.

Furthermore, when a liquid fuel is used, since the liquid fuel is stored in a liquid fuel module and the liquid fuel module is configured to be coupled with or separated from the fuel module chamber of the housing in a drawer manner, filling the fuel may be easier and more convenient. Since an absorbent member, which absorbs a liquid fuel and vaporizes the liquid fuel by receiving heating energy, is configured as an absorbent member module to be coupled with or separated from an absorbent member module chamber of the housing in a drawer manner, replacing the absorbent member which needs regular replacement may be more convenient.

DETAILED DESCRIPTION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Hereinafter, the present invention will be described in detail with reference to the accompanying drawings. However, unless otherwise specified, "heating energy" and "energy" mean "light energy" and "heating" means "irradiation" of light energy.

First Exemplary Embodiment

Figure 1:
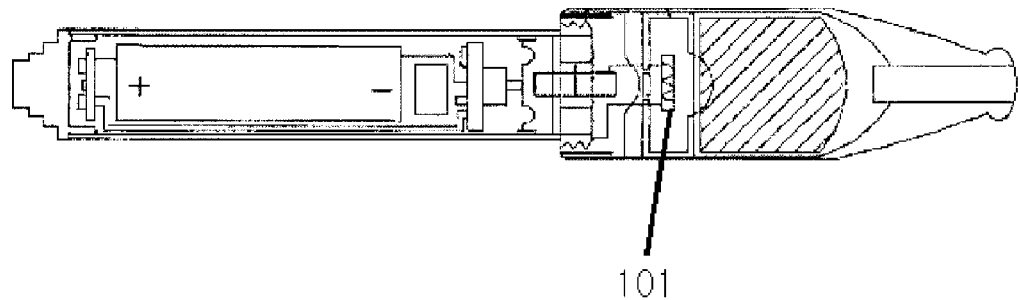
FIGS. 1 and 2 illustrate vaporization devices of electronic cigarettes according to the related art.
Figure 2:
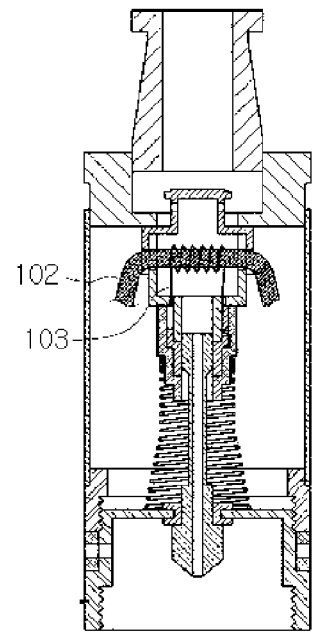
Figure 3:
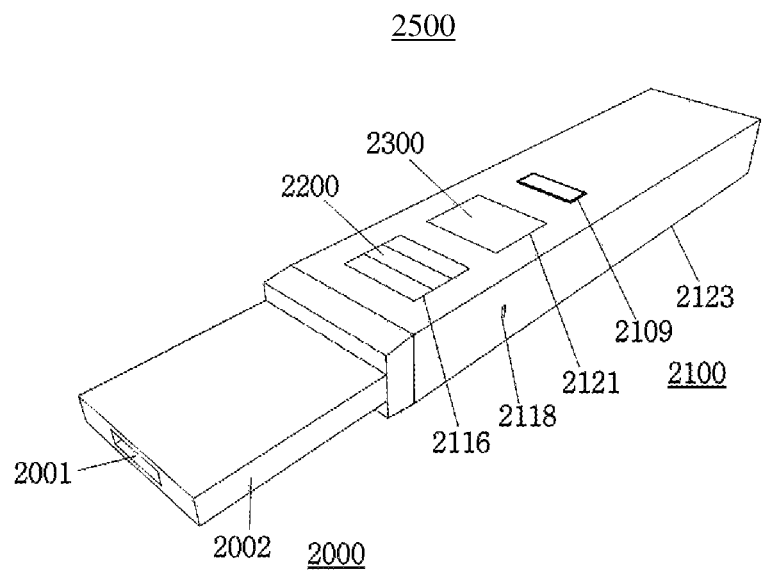
FIG. 3 is a vaporizer according to a first exemplary embodiment of the present invention.
Figure 4:
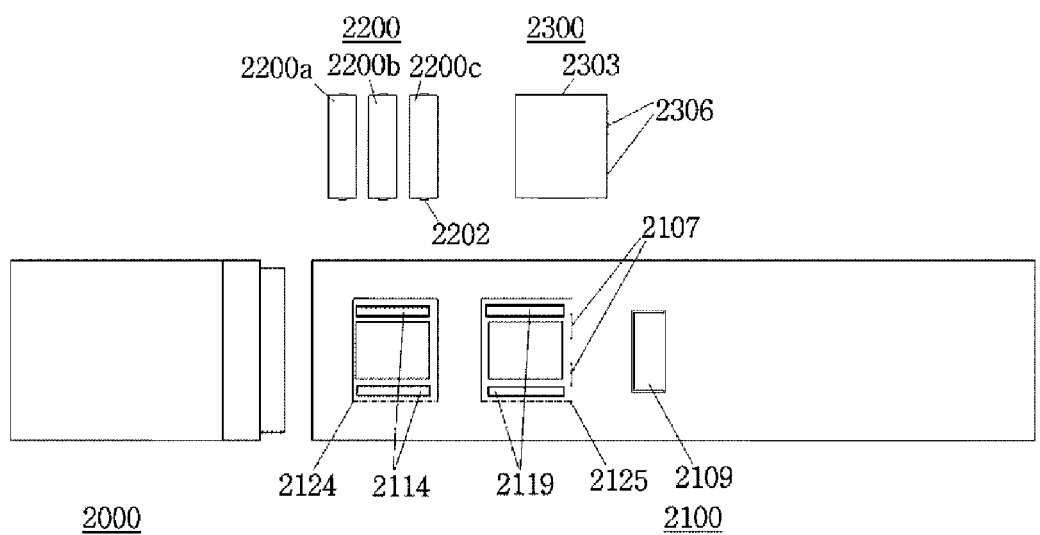
FIG. 4 is an exploded front view illustrating a suction portion, a body portion, a fuel module, and a heating module according to the first exemplary embodiment of the present invention.

A modularized vaporizer 2500 according to a first exemplary embodiment of the present invention will be described with reference to FIGS. 3 and 4. An overall shape thereof may be a quadrangular shape as shown in FIG. 3 and may include a combination of a suction portion 2000 and a body portion 2100. The suction portion 2000 may include a suction aperture 2001 that passes through an inside of a suction body 2002 to discharge a vaporized fuel.

The body portion 2100 may include a fuel module chamber 2124, a heating module chamber 2125, and a button 2109. An air current aperture 2118, through which outside air flows into a vaporization space 2106, may be formed in one part of a side surface of a housing 2123.

In addition, the fuel module chamber 2124 and the heating module chamber 2125 may be configured such that both sides of corresponding parts of the housing 2123 are open. One open surface of the housing 2123 may have a size such that a fuel module 2200 and a heating module 2300 are inserted therein in a drawer manner, and the other open surface thereof may have a size smaller than those of the fuel module 2200 and the heating module 2300 such that the fuel module 2200 and the heating module 2300 are fixed.

Further, magnets 2114 and 2119 may be installed on an inner surface of the fuel module chamber 2124 and the heating module chamber 2125. The surfaces of the fuel module 2200 and the heating module 2300 which come into contact with the magnets 2114 and 2119 may be formed of a material, which can be coupled with a magnet, or may include a magnet to be fixed to the fuel module chamber 2124 and the heating module chamber 2125 by a magnetic force (a magnet may be formed on a coupling part between an edge of an open surface of a module chamber and an open surface of a module or on an external surface of the module chamber). Further, as shown in FIG. 4, the fuel module 2200 and the heating module 2300 may have a quadrangular shape and a plurality of such fuel modules 2200a, 2200b, and 2200c may be included.

Figure 5:
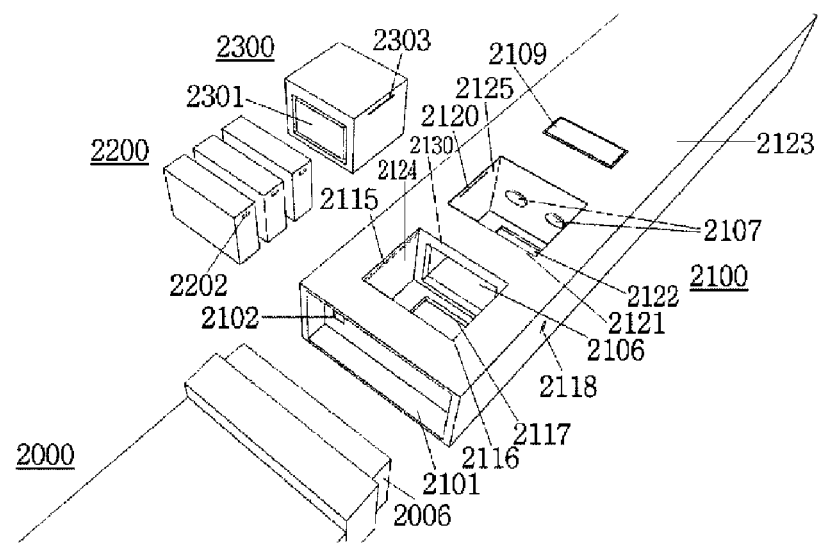
FIG. 5 is a configuration diagram a illustrating the suction portion, the fuel module, a fuel module chamber, the heating module, and a heating module chamber according to the first exemplary embodiment of the present invention.
Figure 6:
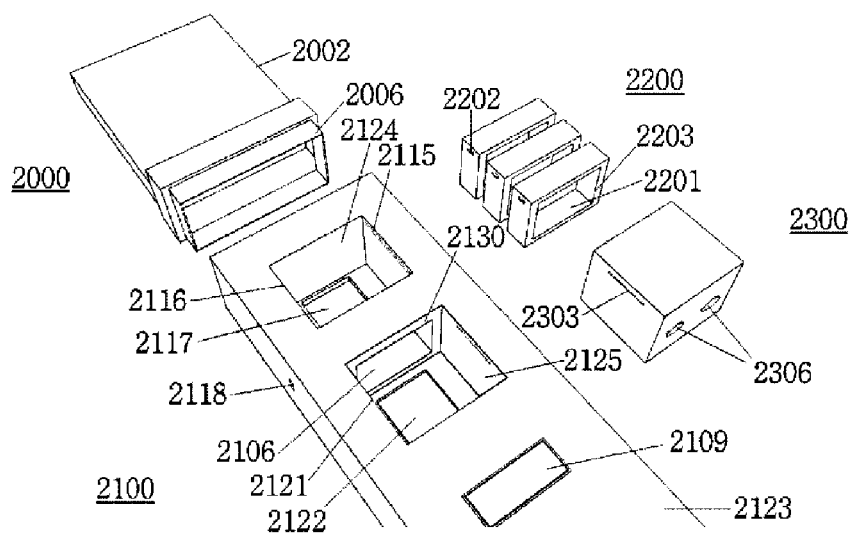
FIG. 6 is a configuration diagram b illustrating the suction portion, the fuel module, the fuel module chamber, the heating module, and the heating module chamber according to the first exemplary embodiment of the present invention.

Based on the above basic structure, an internal structure and a combinational structure of the vaporizer 2500 will be described. First, FIGS. 5 and 6 are views illustrating an internal state in which the suction portion 2000, the fuel module 2200, and the heating module 2300 are separated from one another, from two directions, respectively. A coupling portion 2006 of the suction portion 2000 may be configured to be coupled to or separated from a coupling groove 2101 of the body portion 2100 in a female-and-male manner. An inside of the coupling portion 2006 may be hollow to discharge a vaporized fuel. An air current aperture 2102, through which a vaporized fuel generated in the vaporization space 2106 is discharged, may be formed in one part of a closed surface of the coupling groove 2101.

The fuel module chamber 2124 may be open to both sides of the housing 2123 and include a first open surface 2116 through which the fuel module 2200 enters and a second open surface 2117 to remove the fuel module 2200 which has entered. In the fuel module chamber 2124, a concave line 2115 for fixing the fuel module 2200 may be formed on one part of a sidewall, and an edge 2130 may be formed around the vaporization space 2106 to fix the fuel module 2200.

The fuel module 2200 may have a hollow quadrangular shape in which one surface has the same length as that of the first open surface 2116 of the fuel module chamber 2124 and another surface is open. A hollow part may be configured as a fuel storage space 2201 to store fuel, and an open surface 2203 may be configured to receive heating energy.

Figure 17:
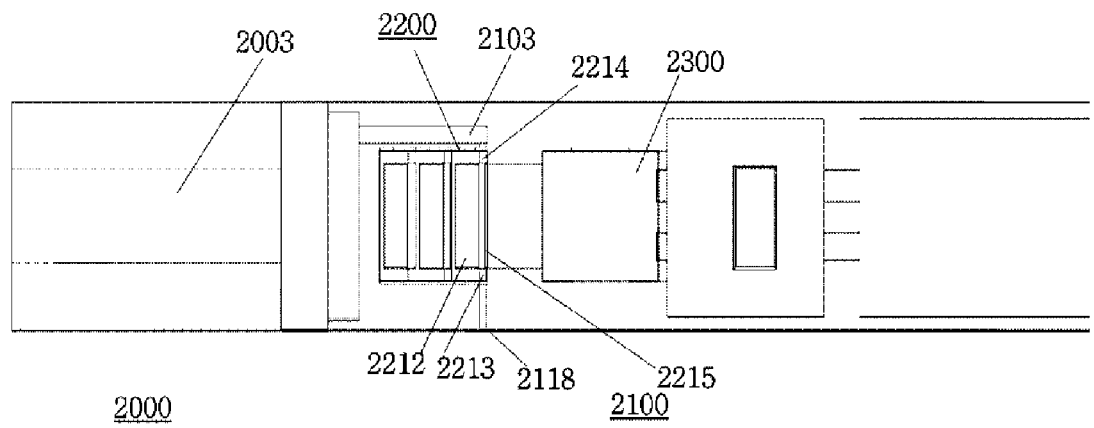
FIG. 17 is a configuration diagram illustrating the fuel module according to the first exemplary embodiment of the present invention.

Referring to FIG. 17, the fuel module 2200 may be configured such that a transmissive member 2215, through which heating energy passes, is formed on one surface receiving heating energy of the heating module 2300, air current apertures a and b 2213 and 2214 are formed in both side surfaces, and the air current apertures a and b 2213 and 2214 horizontally coincide with an air current aperture 2118 of the housing. Outside air, which flows in through the air current aperture 2118 of the housing, may pass through the air current aperture a 2213 of the fuel module 2200, enter an inside of the fuel module 2200, be mixed with fuel 2212 vaporized by the heating energy that has passed through the transmissive member 2215, pass through the air current aperture b 2214, and be discharged through an air current pipe 2103 of the body portion and through an air current pipe 2003 of the suction portion. The transmissive member 2215 for heating energy may be formed as a half mirror (e.g., one-way transmisssive mirror) such that heating energy enters only the inside of the fuel module 2200 and does not escape from the fuel module 2200 to increase efficiency of vaporization.

In addition, a convex line 2202 formed as a line convexly protruding from a side surface of the fuel module 2200 may be included to be coupled with the concave line 2115 formed as a line concavely receding from the fuel module chamber 2124 to fix the fuel module 2200. A coupling between the concave line and convex line may be used both for fixing the module and the module chamber and for watertight sealing therebetween. One or more of such fuel modules 2200 may be provided. A plurality of the fuel modules 2200 may have an advantage of replacing one fuel module with another fuel module by shifting position when fuel thereof is exhausted and accommodating the exhausted fuel module simultaneously.

Figure 16:
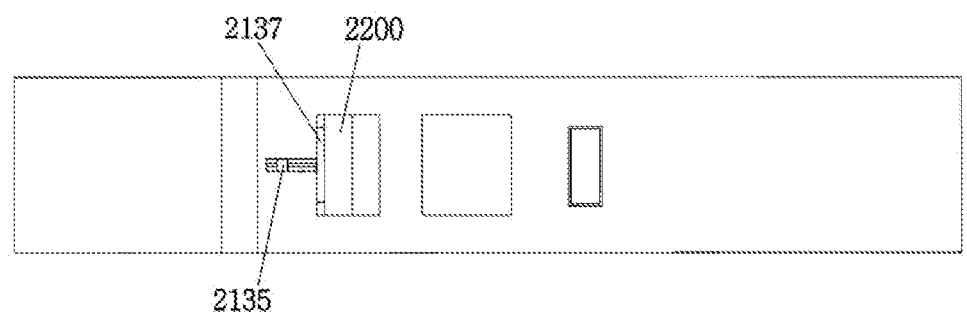
FIG. 16 is an application view illustrating a fixing member according to the first exemplary embodiment of the present invention.

Referring to FIG. 16, instead of a coupling structure of the convex line 2202 and the concave line 2115, on one side surface of an inside of the fuel module chamber 2124, a fixing member 2137 compressing and fixing the fuel module 2200 may be formed by installing an elastic material such as a spring in the housing and may be equally applied to the heating module chamber, an absorbent member module chamber, and the like. Additionally, the fixing member 2137 may be configured to be adjustable in height by hand to correspond to the number of the fuel modules 2200 by forming a button 2135 that adjusts the fixing member 2137, and may be configured to have a shape to accommodate solid fuel (hereinafter, the solid fuel may include natural plant or solidified fuel, which generates a vapor or particles upon receiving light energy) and may be directly filled with the solid fuel. The housing 2123 may further include a protecting cover (not shown) to protect the fixing member button 2135 and the fuel module 2200. Additionally, the button 2135 may be configured as a sliding type, a push type button, or the like.

The heating module chamber 2125 may be open to both sides of the housing 2123 and include a third open surface 2121 through which the heating module 2300 enters and a fourth open surface 2122 to remove the heating module 2300 which has entered. In the heating module chamber 2125, a concave line 2120 for fixing the heating module 2300 may be formed on one part of a sidewall, an edge 2130 may be formed around the vaporization space 2106 to fix the heating module 2300, and electric terminals 2107 may be formed on a surface at a side of the button 2109.

Figure 8:
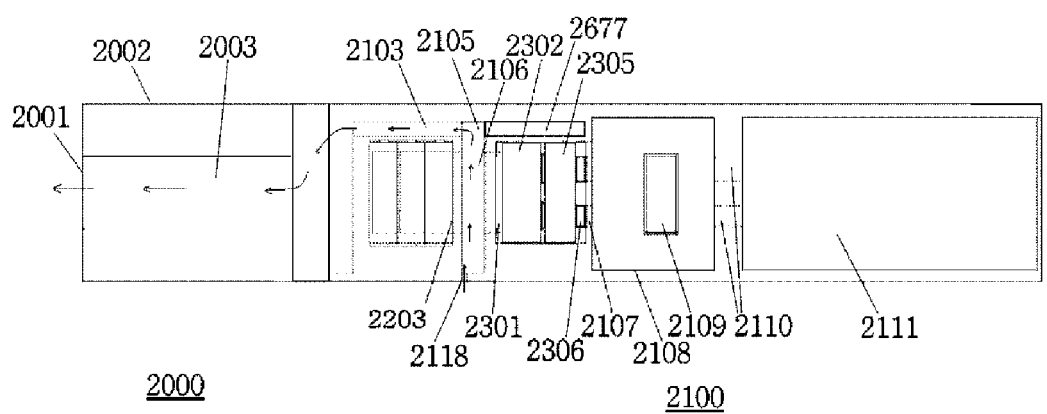
FIG. 8 is an operational view illustrating the vaporizer according to the first exemplary embodiment of the present invention.

Referring to FIG. 8, the heating module 2300 may have a quadrangular shape identical to the third open surface 2121 of the heating module chamber 2125, may include a heating member 2301 formed on a surface in contact with the vaporization space 2106, electric terminals 2306 on a surface opposite to the heating member 2301 to receive power when connected to the electric terminals 2107 of the heating module chamber 2125, a convex line 2303 formed on a side surface which is coupled with the concave line 2120 of the heating module chamber 2125 to fix the heating module 2300, and an internal module 2302 and a circuit board 2305 of the heating module which are coupled with the heating member 2301 therein. The heating member 2301 may be formed as a lamp that emits a laser, infrared rays, ultraviolet rays, a halogen lamp, and the like having a light (beam) property, and may include a heating wire (pipe), which releases heat, or may include a single, a plurality of, or a combination of such laser, infrared, ultraviolet, and halogen lamps or a heating wire (pipe) which are formed as dots, lines, or partial surfaces at a particular part of the heating module 2300.

Figure 7:
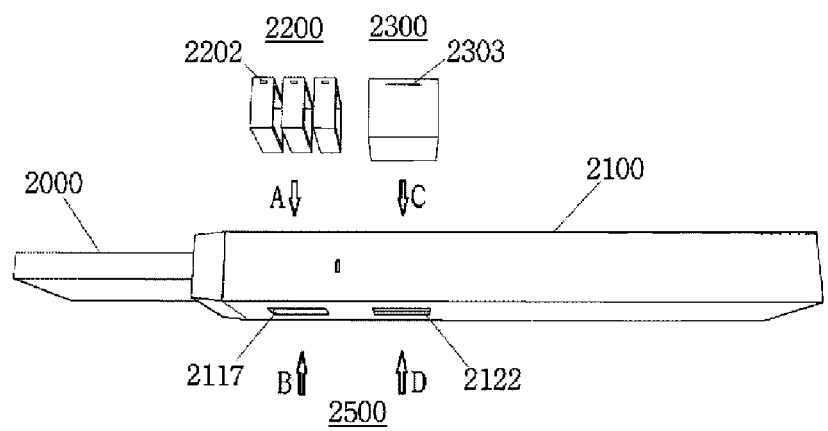
FIG. 7 is a combinational-exploded use view illustrating the fuel module and the heating module according to the first exemplary embodiment of the present invention.

Referring to FIG. 7 for using the modularized vaporizer 2500 configured as described above, the fuel module 2200 may be pushed and inserted into the first open surface 2116 by hand in a direction of an arrow A to couple the fuel module 2200 or may be pushed by hand at the second open surface 2117 in a direction of an arrow B to separate the fuel module 2200.

Similarly, the heating module 2300 may be pushed and inserted into the third open surface 2121 in a direction of an arrow C when the heating module 2300 is coupled with the heating module chamber 2125 or may be pushed through the fourth open surface 2122 with a hand in a direction of an arrow D in order to separate the heating module 2300 therefrom.

In the related art, in order to replace a vaporization device, a component wet with a liquid fuel is replaced by releasing double screw coupling of inside and outside of a cartridge or by releasing a cartridge (fuel storage housing) fastened through a thread-coupling to fill a liquid fuel. Conversely, the coupling or separation in a drawer manner according to the present invention may remove the inconvenience in the related art, and replacement may be performed more easily through a push-in by hand from the outside of the housing 2123.

In addition to replacement of a failed component or filling of fuel, when a plurality of such fuel modules 2200 are provided, the fuel modules 2200 having a variety of components may be stored in the fuel module chamber 2124 to be selected and applied as necessary. Also for the heating module 2300, there is an advantage of selecting by coupling or separating a variety of heating modules 2300 having heating energy with different intensities, different emission areas, and different shapes.

Referring to FIG. 8 illustrating an operation of a vaporizer according to a first exemplary embodiment of the present invention as described above, a battery cell 2111 of the body portion 2100 may be connected to a power module 2108 through a wire 2110. The power module 2108 may be connected to the heating module 2300 through the electric terminals 2306 and 2107.

When the button 2109 of the power module 2108 is pushed and power is applied, the power may be supplied from the battery cell 2111 through the power module 2108 and to the heating module 2300 sequentially to cause the heating member 2301 to emit a heating energy. The power module 2108 may be configured as a button type module or a suction pressure sensor type module. In the case of the suction pressure sensor type module, outside air, which flows in through the air current aperture 2118 (refer to FIG. 3), may be configured to pass through the vaporization space 2106 via the suction pressure sensor type module. Hereinafter, the button type module will be described as an example.

The heating energy emitted by the heating module chamber 2125 may irradiate the fuel module open surface 2203 to vaporize fuel to allow the vaporized fuel to be released in the vaporization space 2106. When suction is applied to the suction aperture 2001 of the suction portion 2000, as arrows in FIG. 8, outside air may flow in through the air current aperture 2118 of the body portion and may be mixed with the vaporized fuel released in the vaporization space 2106. The vaporized fuel mixed with the outside air may be discharged from the vaporization space 2016 to an air current space 2105, the air current pipe 2103 of the body portion, the air current pipe 2003 of the suction portion, and the suction aperture 2001 sequentially.

Figure 9:
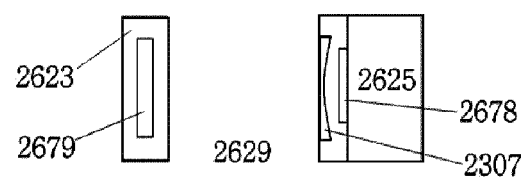
FIG. 9 is an application view illustrating a functional lens of a heating member according to the first exemplary embodiment of the present invention.

In the present invention, use of heating energy may be configured to be restricted to a vaporization device of a vaporizer. As an example, when the heating module 2300 or the housing 2123 includes a sensor therein to detect an object within a vaporization focal length from a heating member and to apply heat generation, since the heating energy is emitted only when the fuel module 2200 is coupled, a human body may be protected from being harmed by the heating energy emitted while the fuel module 2200 is separated, or a device may be protected from the heating energy at a high temperature. Moreover, as shown in FIG. 9, a functional lens 2307 may be coupled to a front surface of a light generation portion 2678 of the heating member 2301 such that a wavelength of heating energy is canceled after a certain distance to prevent the heating energy, which may be used for other than vaporization, from being misused, according to the present invention. In addition, the lens 2307 may be configured to irradiate on an absorbent member or fuel by adjusting light energy (a functional lens of FIG. 9 is not limited to a concave lens and may include a convex or concave part when a heating member includes a plurality of lamps, or may be formed in partial lines or surface shapes), or may be configured to allow achromatic light energy to be visually seen using a colored lens.

Figure 10:
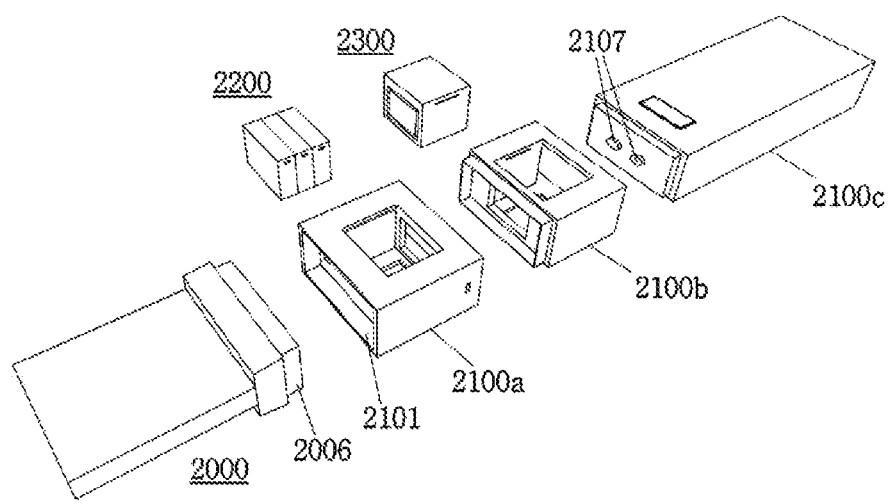
FIG. 10 is an exploded configuration diagram illustrating the body portion according to the first exemplary embodiment of the present invention.

In addition, as shown in FIG. 10, the body portion 2100 may comprise a body portion a 2100a, a body portion b 2100b, and a body portion c 2100c that correspond to a fuel module chamber, a heating module chamber, and a battery portion, respectively, and the body portion a 2100a, the body portion b 2100b, and the body portion c 2100c may be coupled with or separated from one another when washed, replaced, or repaired.

Solid fuel may be produced using the same method as a tablet process or a process of jelly food and the like which is well-known in the art and may be formed by uniformly standardizing and quantifying contents of perfume, polyethylene, glycol, glycerol, sorbitol, antismoking adjuvant, nicotine, an excipient, a bonding agent, a coloring agent, and the like which may be used as elements to prevent a particular element from being excessively mixed. Since fuel is stored in the fuel module 2200 and the open surface 2203 of the fuel module is hygienically packed and distributed as a unit, hygienic management and storage may be achieved, and safety of a fuel product may be secured more reliably.

Since the above-described solid fuel manner includes a structure unable to be achieved using a conventional heating wire manner in the related art, the solid fuel manner may be a feature of the present invention in which heating energy is emitted toward fuel (or an absorbent member) while being in non-contact with the fuel (or the absorbent member) and spaced apart therefrom, and inconvenience such as external pollution and the like caused by a leakage due to use of a conventional liquid fuel may be eliminated. The first exemplary embodiment of the present invention may be used for a hard solid fuel, a soft jelly type fuel, and the soft fuel that may be manufactured using a well-known method, and thus, a detailed description of the method will be omitted.

Second Exemplary Embodiment

Figure 11:
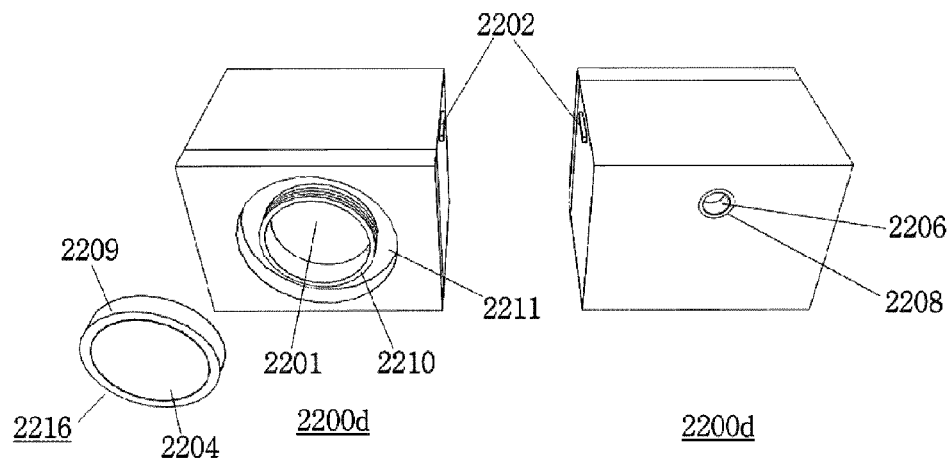
FIG. 11 is a configuration diagram illustrating a rechargeable liquid fuel module according to a second exemplary embodiment of the present invention.

Hereinafter, a modularized vaporizer using a liquid fuel will be described. First, FIG. 11 illustrates a part receiving heating energy of a liquid fuel module 2200d and a part through which a liquid is injected.

The liquid fuel module 2200d may have a hollow quadrangular shape within which a liquid fuel is stored. A circular coupling portion 2210 having a thread (e.g., spiral line) may be formed on one surface to make an absorbent member 2204 replaceable. A free space 2211 may be formed on an outer circumferential surface of the coupling portion 2210 to facilitate rotating the absorbent member member module 2216. An inlet 2206 may be formed in another surface to fill a liquid fuel, and an elastic member 2208 having a sealing (waterproof) function may be disposed on an edge of the inlet 2206.

Further, the absorbent member 2204 may be formed of a heat-resistant material (glass fiber, cotton, Korean traditional paper, natural lumber, natural stone, a heat-resistant carbon-processed material, a heat-resistant alloy, and the like or a combination thereof) and may be configured to be fixed to a coupling portion 2209 having a thread on a circular edge thereof to be coupled with or separated from the liquid fuel module 2200d and to periodically replace the absorbent member 2204 from the liquid fuel module 2200d.

Figure 12:
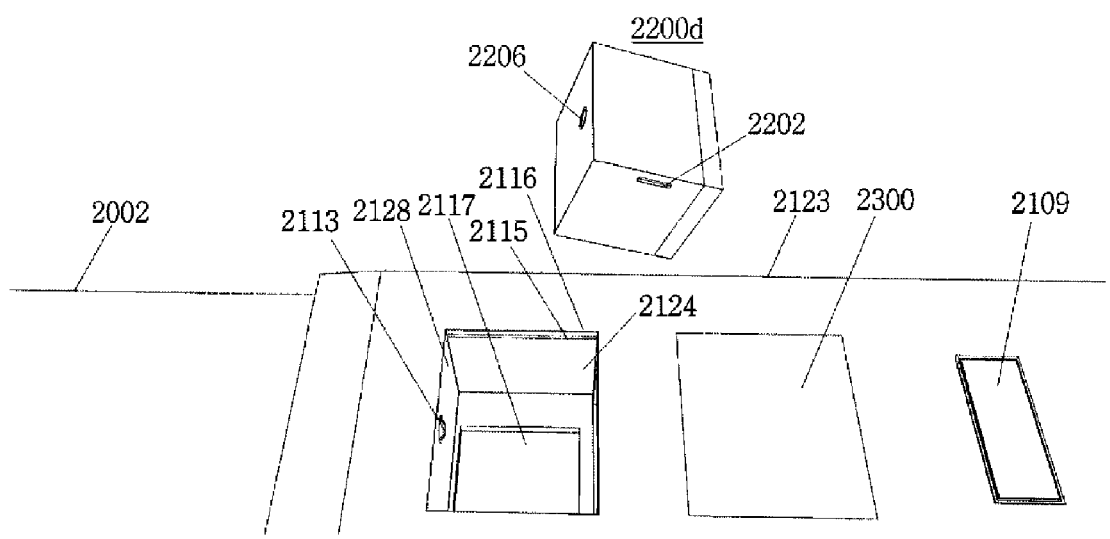
FIG. 12 is a configuration diagram illustrating the rechargeable liquid fuel module and a fuel module chamber according to the second exemplary embodiment of the present invention.

As shown in FIG. 12, like the first exemplary embodiment, the liquid fuel module 2200d may be coupled with or separated from the fuel module chamber 2124 in a drawer manner. In particular, corresponding to the inlet 2206 of the liquid fuel module 2200d, a semicircular inlet stopper 2113 may be formed on one surface of the fuel module chamber 2124 such that the inlet stopper 2113 closes the inlet 2206 to seal or make the liquid fuel module 2200d waterproof when the liquid fuel module 2200d is coupled with the fuel module chamber 2124. The inlet stopper 2113 may have a spherical shape. A half of the spherical shape may be exposed to the fuel module chamber 2124, and the other half may be fixed to an inside of the housing. The inlet stopper 2113 may be fixed to the inside of the housing by an elastic member (not shown) such as a spring.

Figure 13:
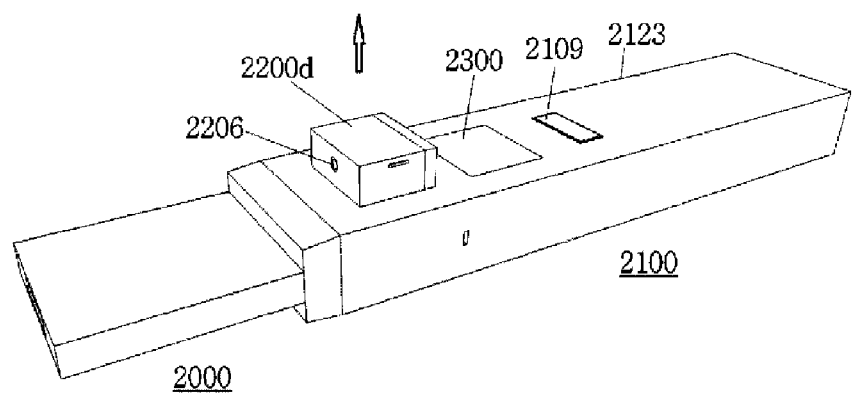
FIG. 13 is a combinational-exploded use view illustrating the rechargeable liquid fuel module according to the second exemplary embodiment of the present invention.
Figure 14:
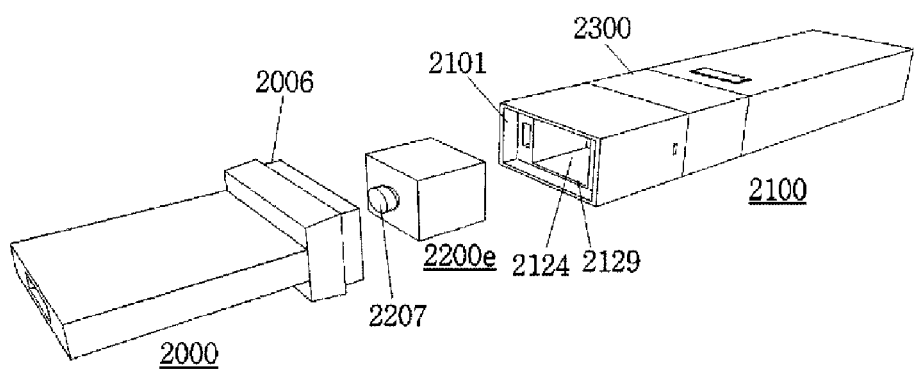
FIG. 14 is a configuration diagram illustrating a fuel module and a fuel module chamber according to a third exemplary embodiment of the present invention.

Referring to FIG. 13 for use of the second exemplary embodiment configured as described above, in order to fill a liquid fuel, the liquid fuel module 2200d may be pushed in a direction of an arrow to expose the inlet 2206 at the second open surface 2117, filled with fuel (liquid), and pushed again into the fuel module chamber 2124 in a drawer manner.

Additionally, the inlet 2206 for filling fuel and the inlet stopper 2113 are merely an example, and are not limited to a circular or spherical shape. The inlet 2206 and the inlet stopper 2113 may have various shapes in which an open surface is formed on a fuel module to fill fuel and a structure closing the open surface is formed at a fuel module chamber in terms of the coupling structure in a drawer manner. To prevent heating energy from being emitted while the liquid fuel module 2200d is removed, a heating energy absorbent member 2128 may be formed on a surface of the inside of the fuel module chamber 2124 capable of receiving the heating energy to prevent a risk caused by reflection and the like of the heating energy.

Third Exemplary Embodiment

In the present invention, coupling or separating a fuel module with or from a housing in a drawer manner may be performed by separating the suction portion 2000 from the body portion 2100 and inserting a fuel module 2200e into a fifth open surface 2129 of the fuel module chamber 2124 included in the body portion 2100.

In coupling and separating between the fuel module 2200e and the fuel module chamber 2124, like the first exemplary embodiment, the coupling structure may include a magnet, a structure of a concave line and a convex line, or the like. The fuel module 2200e is not limited to a solid or liquid fuel and may include a handle 2207 on one surface thereof to be coupled or separated more easily.

Fourth Exemplary Embodiment

A fourth exemplary embodiment of the present invention may include a fuel chamber having an inlet for filling and a cover, and may include a configuration in which an absorbent member may be replaced more easily.

When an absorbent member 2401, in which absorption and vaporization of fuel occur, is exposed to heating energy at a high temperature for an extended period, since a material thereof is cured and an absorption rate of a liquid fuel is decreased or the absorbent member 2401 is aged such that the liquid fuel may leak, periodic replacement of the absorbent member 2401 may be necessary. Accordingly, an absorbent member module 2400, to which the absorbent member 2401 is fixed, may be configured to be coupled or separated in a drawer manner from the outside.

Figure 15:
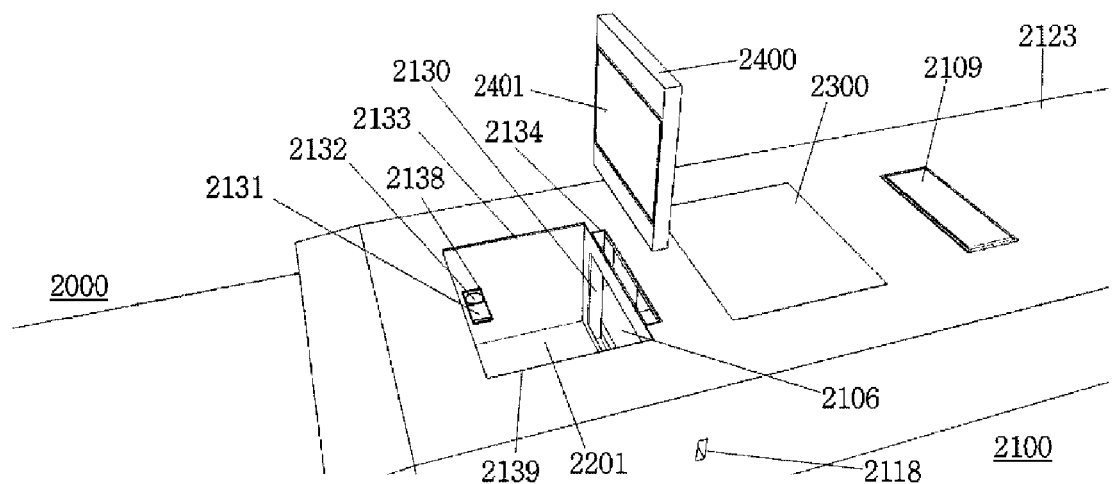
FIG. 15 is a configuration diagram illustrating an absorbent member module and an absorbent member module chamber according to a fourth exemplary embodiment of the present invention.

As shown in FIG. 15, a fuel chamber 2139 of the body portion 2100 may include a transparent member 2133 to provide a view inside the fuel storage space 2201. An inlet 2132 and a cover 2131 that opens or closes the inlet 2132 may be formed inside a sliding frame 2138 at a portion of the transparent member 2133. An elastic body (spring) or a magnetic body (magnet) may be formed between the cover 2131 and the transparent member 2133 to allow the inlet 2132 to be opened for filling while remaining closed by the cover 2131 when not filling.

Positions of the inlet 2132 and the cover 2131 are not limited to the transparent member 2133 and may be formed on the housing 2123 around the transparent member by connecting a pipe to the fuel chamber 2139. In this way, a flow of stored fuel may be adjusted by controlling a pressure in the liquid fuel module by forming one or more air current apertures smaller than the inlet 2132 and by opening or closing the air current apertures using the covers.

In addition, one surface of the inside of the fuel chamber 2139 may be open to the vaporization space 2106. An absorbent member module chamber 2134 may be formed between the fuel chamber 2139 and the vaporization space 2106. In order to adjust the pressure in the fuel chamber 2139, an air current aperture (not shown) that passes through the fuel chamber 2139 may be additionally formed in the transparent member 2133 or the housing 2123. Further, the absorbent member module chamber 2134 may be open to both sides of the housing 2123 such that the absorbent member module 2400 may be coupled with or separated from the absorbent member module chamber 2134 in a drawer manner. The absorbent member module 2400 may have a quadrangular shape, and the absorbent member 2401 may be fixed to a central part thereof.

A method of coupling and separating the absorbent member module 2400, like the fuel module 2200 and the heating module 2300 of the first exemplary embodiment in general, may include coupling or separating the absorbent member module 2400 with or from the absorbent member module chamber 2134 using a push by hand.

Fifth Exemplary Embodiment

A fifth exemplary embodiment of the present invention may include a configuration in which a vaporization module 2602 is coupled with or separated from, in a drawer manner, a vaporization module chamber 2611 open to both sides of a housing 2608 of the body portion 2100. Further, an absorbent member module 2630 and a heating module 2631 separately provided from each other may be coupled with or separated from an absorbent member module chamber 2639 and a heating module chamber 2640 open to both sides of the vaporization module 2602 in a drawer manner.

Figure 18:
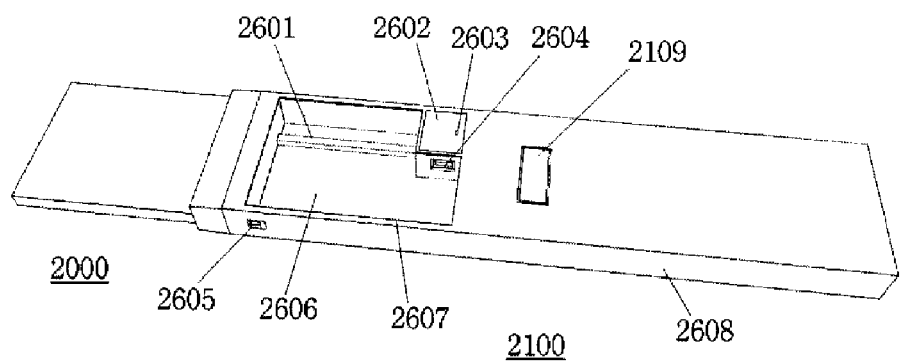
FIG. 18 is a vaporizer according to a fifth exemplary embodiment of the present invention.
Figure 19:
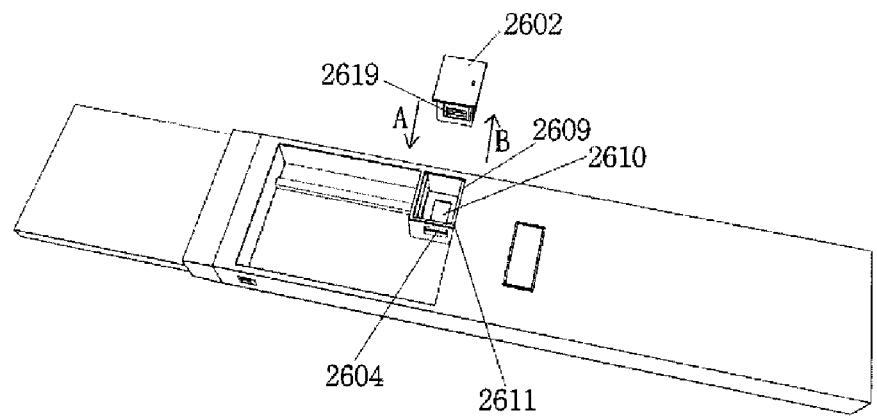
FIG. 19 is a combinational-exploded use view illustrating a vaporization module according to the fifth exemplary embodiment of the present invention.

FIG. 18 illustrates a state in which the vaporization module 2602 is coupled with the vaporization module chamber 2611, and FIG. 19 illustrates a state in which the vaporization module 2602 is separated from the vaporization module chamber 2611. The vaporization module 2602 may be inserted into a sixth open surface 2609 of the vaporization module chamber 2611 in a direction of an arrow A. When the vaporization module 2602 is pushed through a seventh open surface 2610 of the vaporization module chamber 2611 in a direction of an arrow B, the vaporization module 2602 may be separated from the vaporization module chamber 2611.

Figure 20:
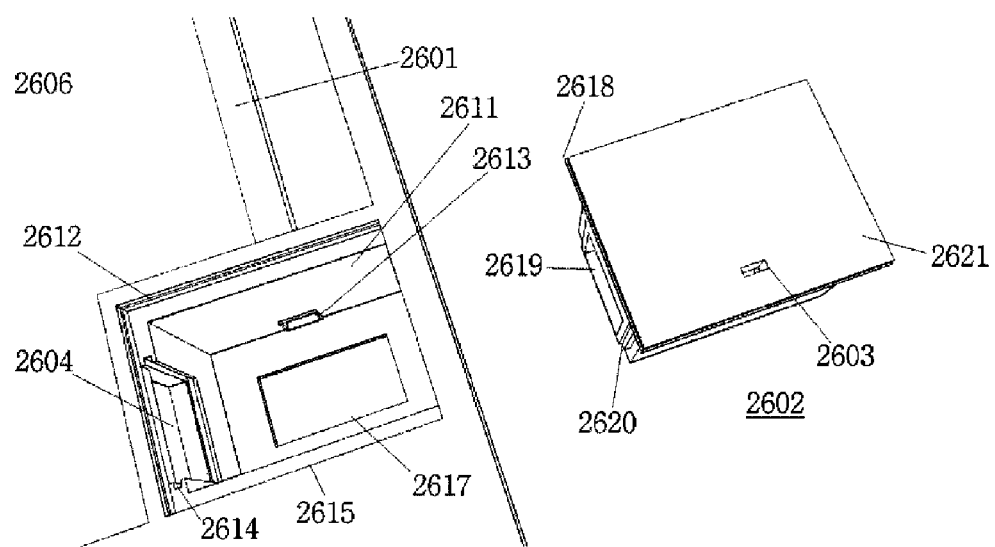
FIG. 20 is a partial view illustrating the vaporization module and a vaporization module chamber according to the fifth exemplary embodiment of the present invention.

A detailed configuration of coupling and separation between the vaporization module 2602 and the vaporization module chamber 2611 will be described with reference to FIG. 20. The vaporization module chamber 2611 may be open to both sides of the body portion housing 2608 to allow the vaporization module 2602 to be inserted into one part of a fuel chamber 2607. The sixth open surface 2609, into which the vaporization module 2602 is inserted, and the seventh open surface 2610 for separating the vaporization module 2602 may include stepped edges, and waterproof concave lines 2612 may be formed on the stepped edges to form a water-tight coupling with waterproof convex lines 2618 of coupling panels a and b 2621 and 2635 of the vaporization module 2602 (coupling between the waterproof concave lines and the waterproof convex lines are used for waterproofness and for fixation of the module to the module chamber).

A fuel transfer aperture a 2604, through which fuel of a fuel storage space 2606 moves to the vaporization module chamber 2611, may be formed on one surface of an inside of the vaporization module chamber 2611.

A depression coupling portion 2614, which is connected to the fuel transfer aperture a 2604 and includes an open center and three partially concave edges, may be formed at the stepped part of the sixth open surface 2615 for a water-tight coupling with a protruding coupling portion 2620 which includes a center open to one outer surface of the vaporization module 2602 and three partially convex edges.

A depression coupling portion 2613, which is connected to an air current pipe 2601 that discharges a vapor into the suction portion 2000 and includes an open center and three partially concave edges, may be formed on another surface of the inside to form a water-tight coupling with a protruding coupling portion 2634 (refer to FIG. 22) which includes a center open to one outer surface of the vaporization module 2602 and three partially convex edges to discharge a vapor generated by the vaporization module 2602. An electric terminal (not shown), which connects power of a battery cell to the vaporization module 2602, may be formed on still another surface of the inside.

Figure 21:
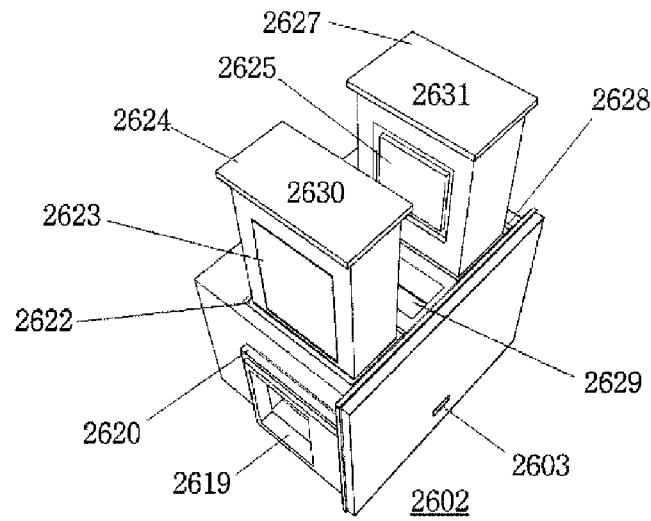
FIG. 21 is a perspective view illustrating the vaporization module according to the fifth exemplary embodiment of the present invention.
Figure 22:
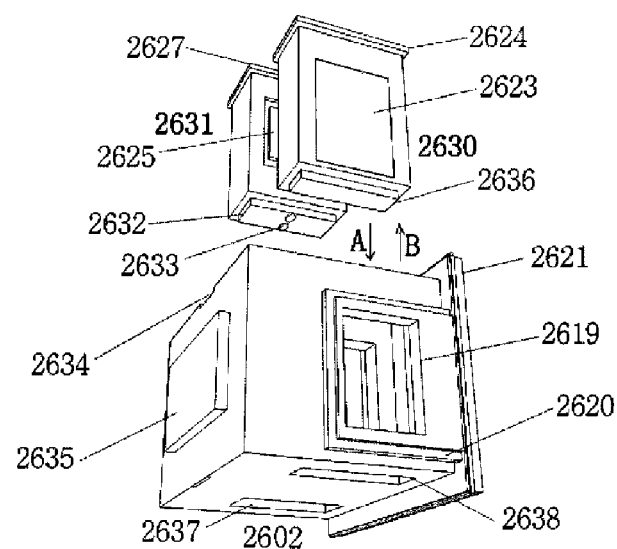
FIG. 22 is another perspective view illustrating the vaporization module according to the fifth exemplary embodiment of the present invention.

A detailed configuration of the vaporization module 2602 will be described with reference to FIGS. 21, 22, and 23. The vaporization module 2602 may have a quadrangular shape and may include, on two outer surfaces, the coupling panels a and b 2621 and 2635 which forms a water-tight coupling with the stepped edges of the sixth and seventh open surfaces 2615 and 2617. The waterproof convex lines 2618 may be formed on edges of the coupling panels a and b 2621 and 2635 to form a water-tight coupling with the waterproof concave lines 2612 of the sixth and seventh open surfaces 2615 and 2617. An air current aperture 2603 may be formed in a part of surfaces of the coupling panels a 2621 or b 2635 to allow outside air to flow into a vaporization space 2629.

The protruding coupling portion 2620, which includes an open center and three partially convex edges which protrude, may be formed on another outer surface to form a water-tight coupling with the depression coupling portion 2614 formed on the stepped edge of the sixth open surface 2615 of the vaporization module chamber 2611.

The protruding coupling portion 2634, which includes an open center and three partially convex edges, may be formed on still another outer surface and may be connected to the air current pipe 2601 on one surface of the inside of the vaporization module chamber 2611 to form a water-tight coupling with the depression coupling portion 2613 having three partially concave edges which protrude. An electric terminal may be formed on still another outer surface to be connected to an electric terminal formed on one surface of the inside of the vaporization module chamber 2611.

In the vaporization module 2602, a fuel transfer aperture b 2619 into which fuel of the fuel chamber 2607 flows, the absorbent member module chamber 2639 into which the absorbent member module 2630 is inserted, the vaporization space 2629, and the heating module chamber 2640 into which the heating module 2631 is inserted may be sequentially opened. An open channel a 2654 may be formed between the absorbent member module chamber 2639 and the vaporization space 2629, and an open channel b 2655 may be formed between the vaporization space 2629 and the heating module 2631. The protruding coupling portion 2634 that releases a generated vapor may be formed on a part of an inner wall of the vaporization space 2629.

The absorbent member module chamber 2639 and the heating module chamber 2640 may be formed such that both sides of a housing of the vaporization module 2602 are open. An eighth open surface 2622 and a ninth open surface 2638 through which an absorbent member module 2630 is inserted into and separated from the absorbent member module chamber 2639 in a drawer manner may include stepped edges. A tenth open surface 2628 and an eleventh open surface 2637 through which the heating module 2631 is inserted into and separated from the heating module chamber 2640 in a drawer manner may include stepped edges.

The absorbent member module 2630 and the heating module 2631 which are coupled with or separated from the vaporization module 2602 will be described. The absorbent member module 2630 may have a quadrangular shape and include coupling panels c and d 2624 and 2636 on two outer surfaces to form a water-tight coupling with the stepped edges of the eighth and ninth open surfaces 2622 and 2638 of the absorbent member module chamber 2639. Waterproof convex lines may be formed on edges of the coupling panels c and d 2624 and 2636 to form a water-tight coupling with waterproof concave lines of the eighth and ninth open surfaces 2622 and 2638, and an absorbent member 2623 may be inserted thereinto. The absorbent member 2623 may include glass fiber, cotton, Korean traditional paper, natural lumber, natural stone, a heat-resistant carbon-processed material, a heat-resistant alloy, and the like, or a combination thereof to absorb and store fuel or discharge fuel of the fuel chamber 2607 by, for example, osmosis.

The heating module 2631 may have a quadrangular shape and include coupling panels e and f 2627 and 2632 on two outer surfaces to form a water-tight coupling with the stepped edges of the tenth and eleventh open surfaces 2628 and 2637. Waterproof convex lines may be formed on edges of the coupling panels e and f 2627 and 2632 to form a water-tight coupling with waterproof concave lines of the tenth and eleventh open surfaces 2628 and 2637. An electric terminal 2633 may be formed on another surface of an outside and connected to an electric terminal formed on one surface of the inside of the vaporization module chamber 2611, and a heating member 2625 may be formed inside the heating module 2631. The heating member 2625 may include one, a plurality, or a combination of a laser beam lamp, an infrared lamp, an ultraviolet lamp, a halogen lamp, and a heating wire (pipe) and may have a shape such as a dot, a line, and a surface (or a plurality of dots, lines, and surfaces).

According to the above-described configuration, an operational method of the fifth exemplary embodiment will be described with reference to FIGS. 18 and 23. Fuel injected into a fuel inlet 2605 may move to the absorbent member 2623 of the absorbent member module 2630 through the fuel transfer aperture a 2604 of the fuel chamber 2607 and the fuel transfer aperture b 2619 of the vaporization module 2602. When power is applied to the heating module 2631 by pushing the button 2109 of the body portion 2100, the heating member 2625 may emit energy (light, beams, and heat) toward the absorbent member 2623, vaporize the stored fuel to release a vapor into the vaporization space 2629. When the suction portion 2000 draws air in, the air may flow into the air current aperture 2603 of the vaporization module 2602, be mixed with the vaporized fuel (vapor) in the vaporization space 2629, and be discharged to the air current pipe 2601 and the suction portion 2000 through the open protruding coupling portion 2634 of the vaporization space 2629 and the depression coupling portion 2613 of the vaporization module chamber 2611.

Figure 24:
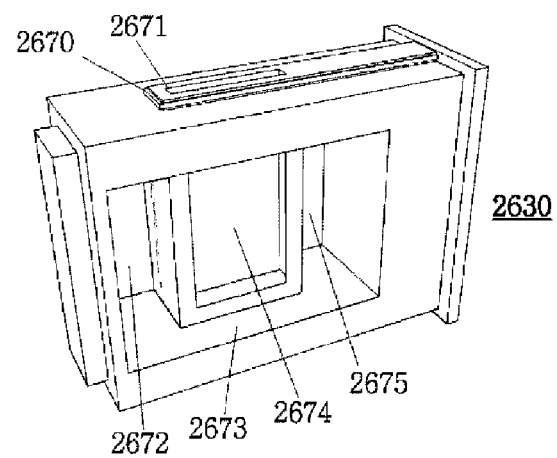
FIG. 24 is a configuration diagram illustrating an absorbent member module including an air current aperture according to the fifth exemplary embodiment of the present invention.
Figure 25:
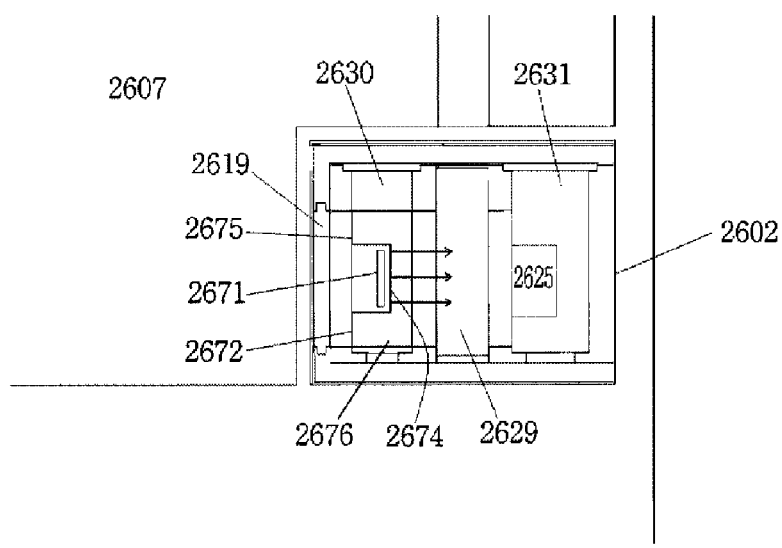
FIG. 25 is an application view illustrating the absorbent member module including the air current aperture according to the fifth exemplary embodiment of the present invention.

A drawer type vaporization module or absorbent member module may be formed to supply fuel more easily from a fuel chamber to an absorbent member using a flowing force of an air current passing through the absorbent member. Referring to FIGS. 24 and 25, the absorbent member module 2630 may include fuel transfer apertures c and d 2672 and 2675 through which the fuel of the fuel chamber 2607 moves to an absorbent member 2676. Between the fuel transfer apertures c and d 2672 and 2675, an air current path may be blocked from the fuel chamber 2607 and connected to an external air current aperture 2671 and a surface, into which the absorbent member 2676 is inserted, may be opened.

An internal air current aperture 2674 may be formed to allow outside air flowing into the external air current aperture 2671 to flow while passing through the absorbent member 2676. An absorbent member accommodation groove 2673, into which the absorbent member 2676 is insertable, may be formed near an open surface area of the internal air current aperture 2674 and the fuel transfer apertures c and d 2672 and 2675.

In order to fix the absorbent member 2676 inserted in the absorbent member accommodation groove 2673, a cover (not shown) having an open part to allow fuel or a vapor to pass therethrough may be inserted into an open surface of the absorbent member accommodation groove 2673. The external air current aperture 2671 may include a protruding coupling portion 2670 having three partially convexly protruding edges to form a water-tight coupling with an air current aperture including a depression coupling portion (not shown) of the vaporization module 2602.

Referring to FIG. 25 for an operation of the vaporization module 2602 configured as described above, the fuel of the fuel chamber 2607 may be absorbed by and stored in the absorbent member 2676 inserted in the absorbent member accommodation groove 2673 through the fuel transfer aperture b 2619 of the vaporization module 2602 and the fuel transfer apertures c and d 2672 and 2675 of the absorbent member module 2630.

When the suction portion 2000 draws air, outside air flowing into the external air current aperture 2671, as shown by arrows in FIG. 25, may pass through the internal air current aperture 2674 and the absorbent member 2676 and flow toward the vaporization space 2629. Due to a flow or a flowing force of air which suctions the absorbent member 2676, the fuel of the fuel chamber 2607 or the fuel of the fuel transfer apertures c and d 2672 and 2675 may flow toward the absorbent member 2676 adjacent to the internal air current aperture 2674 to allow the fuel to be continuously supplied to a surface of the absorbent member 2676 which receives heating energy from the heating member 2625.

Figure 26:
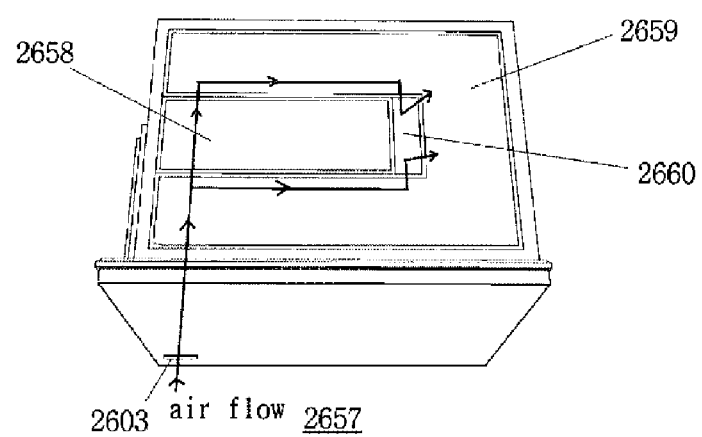
FIG. 26 is a configuration diagram illustrating a heating module, which heats multiple surfaces of an absorbent member according to the fifth exemplary embodiment of the present invention.

Further, in order to further increase efficiency of vaporization, the absorbent member 2623 may be formed to receive heating energy on a plurality of facets. As an exemplary embodiment having the above configuration, referring to FIG. 26, a heating module 2659 may surround an absorbent member module 2658 inserted into a vaporization module 2657 to allow an absorbent member to receive energy on a larger area of two or three surfaces. An air current path may be formed to allow an air current to flow between the absorbent member and the heating member as a direction of an arrow. When heating energy includes a lamp having a single light (beam), the light may be emitted toward two surfaces or three surfaces using a reflector and the like. Positions of the absorbent member module 2658 and the heating module 2659 may be shifted such that energy is emitted from both sides of the heating member and is received by the absorbent member that surrounds the heating member. Two or more staple-shaped (e.g., U-shaped) modules that surround one member may be provided (additionally, the present invention may include a plurality of heating members, which heat one absorbent member on both sides, or may include a plurality of vaporization modules each including an absorbent member and a heating member). Moreover, when heating energy irradiates several surfaces of an absorbent member, each surface of the absorbent member may be independently heated and vaporized, a plurality of pieces of heating energy transmitted into the absorbent member may reach a vaporizing temperature competitively, and thus, a higher efficiency of vaporization may be achieved by complementing of heating energy.

Figure 33:
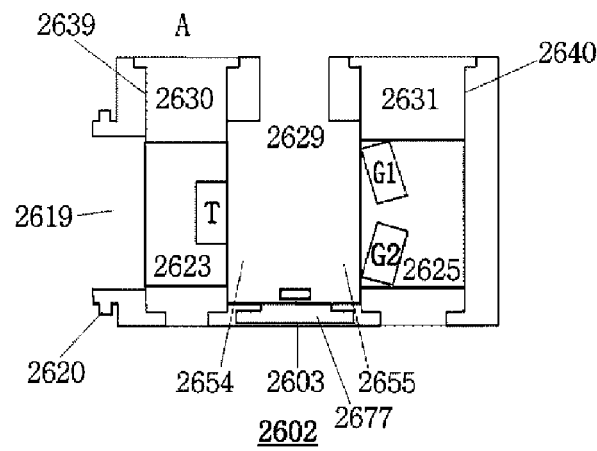
FIG. 33 is a competitive configuration diagram illustrating a plurality of heating energy generation portions according to the present invention.
Figure 34:
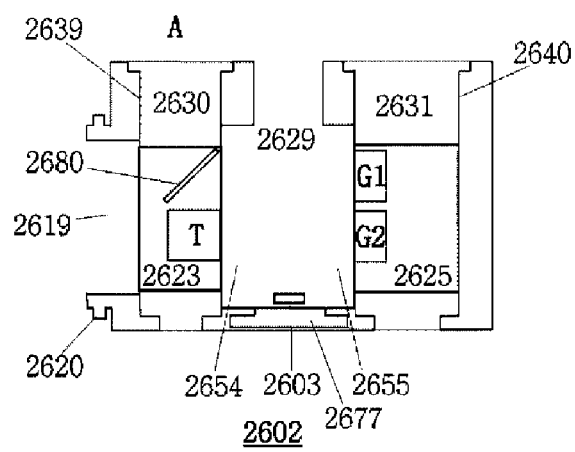
FIG. 34 is another competitive configuration diagram illustrating the plurality of heating energy generation portions according to the present invention.

Another exemplary embodiment having the above configuration will be described with reference to FIGS. 33 and 34. As shown in FIG. 33, toward a target point T of an absorbent member, heating energy generation portions G1 and G2 of a heating member may be formed at a slanted angle such that portions of energy emitted by G1 and G2 may intersect each other and may compete with each other at the point T. In particular, the portions of heating energy emitted by G1 and G2 may compete with each other to achieve a heating temperature, or the heating energy emitted by G1 may be used and G2 may be optionally activated to generate a stronger vaporizing energy. In addition, as shown in FIG. 34, a heating energy generation portion G2 of a heating member horizontally corresponding to a target point T of an absorbent member may be provided, a reflector 2680 may be formed near the target point T of the absorbent member, and a heating energy generation portion G1 of the heating member horizontally corresponding to the reflector may be provided. Heating energy emitted by G2 and heating energy emitted by G1 via the reflector 2680 of the absorbent member may competitively form a heating temperature or may generate a stronger vaporizing energy optionally. Similarly, two or more heating energy generation portions G and reflectors may be formed. The competitive configuration of the heating energy generation portion may be applicable to all of the exemplary embodiments of the present invention.

Figure 27:
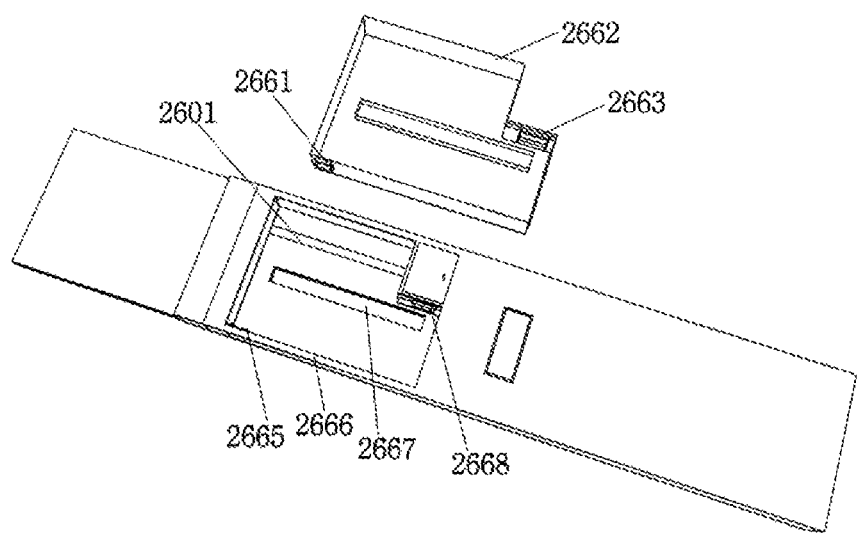
FIG. 27 is an exploded view illustrating a fuel module chamber and a fuel module according to the fifth exemplary embodiment of the present invention.

Referring to FIG. 27, a fuel chamber may be formed as a fuel module 2662 to be coupled with or separated from fourteenth and fifteenth open surfaces 2666 and 2667 open to both sides of a housing. In the above-described configuration of the fuel module 2662, depression coupling portions 2665 and 2668 which include open centers and three partially concave edges which protrude may be formed at the fuel inlet 2605 and the fuel transfer aperture a 2604, respectively. Protruding coupling portions 2661 and 2663 which include open centers and three partially convex edges may be formed at the fuel module 2662 to form a water-tight coupling with the depression coupling portion 2665 and 2668.

Figure 23:
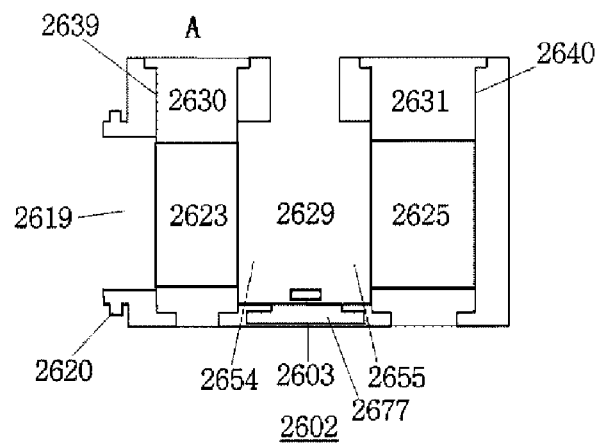
FIG. 23 is a cross-sectional view illustrating the vaporization module according to the fifth exemplary embodiment of the present invention.

In addition, the fuel transfer aperture a 2604 and the fuel transfer aperture b 2619 of the housing may be formed in a direction A of FIG. 23. Existing fuel transfer apertures a and b may have closed structures and may include reflecting plates such that light energy emitted by a heating member is transmitted through an absorbent member and then reflected by the reflecting plates to secondarily heat the absorbent member (hereinafter, a fuel module or a vaporization module of a sixth exemplary embodiment, to which an absorbent member is attached, may include a reflecting plate).

Sixth Exemplary Embodiment

The sixth exemplary embodiment of the present invention may include a configuration in which a fuel chamber is omitted, and a fuel module stores fuel and is coupled with or separated from a vaporization module in a drawer manner. The above-described configuration may be used with a solid type fuel such as a solid, a gel, herbs, tobacco leaves, and the like. When a liquid fuel is applied, an absorbent member may be coupled with a fuel module open surface that receives heating energy or with fuel to prevent an outflow of a solid or a liquid.

Figure 28:
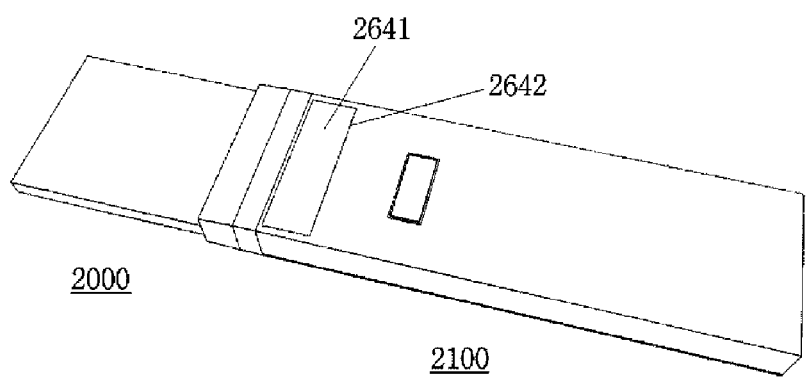
FIG. 28 is a vaporizer according to a sixth exemplary embodiment of the present invention.
Figure 29:
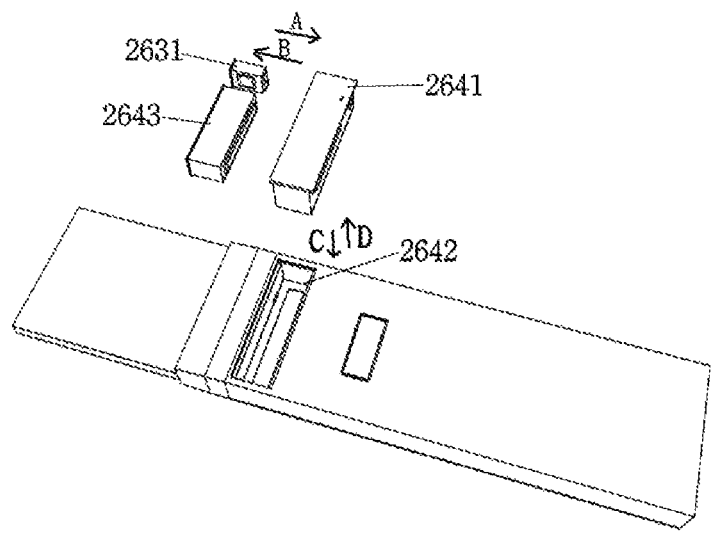
FIG. 29 is a combinational-exploded use view illustrating a vaporization module, a fuel module, and a heating module according to the sixth exemplary embodiment of the present invention.

FIG. 28 illustrates a state in which a vaporization module 2641 is coupled with a vaporization module chamber 2642 of the body portion 2100, and FIG. 29 illustrates a state in which the vaporization module 2641 is separated from the vaporization module chamber 2642, and the heating module 2631 and a fuel module 2643 are separated from the vaporization module 2641. The fuel module 2643 and the heating module 2631 may be coupled with the vaporization module 2641 in a direction of an arrow A, and separated from the vaporization module 2641 in a direction of an arrow B in FIG. 29. The vaporization module 2641 may be coupled with the vaporization module chamber 2642 in a direction of an arrow C, and separated from the vaporization module chamber 2642 in a direction of an arrow D.

A detailed configuration and operational method of the sixth exemplary embodiment is similar to the technical concept of the waterproof-coupling and separation among the absorbent member module 2630, the heating module 2631, and the vaporization module 2602 in the drawer manner of the fifth exemplary embodiment. However, the absorbent member module 2630 may be included in the fuel module 2643, and the fuel chamber 2607 may be omitted to allow a size to be reduced and a solid fuel to be applicable.

An internal configuration of the fuel module 2643 having a quadrangular shape will be described with reference to FIG. 30. A fuel support 2647, with which an elastic member 2646 having elasticity such as a spring is coupled, may be formed on one part within the fuel module 2643. Fuel 2648 may be stored in an internal space excluding the fuel support 2647. An outer surface in surface contact with the channel a 2654 may be formed as a fuel module open surface 2656 which is open. When heating energy emitted by the heating member 2625 vaporizes fuel through the fuel module open surface 2656, a vapor may be released in the vaporization space 2629 and be discharged into the suction portion 2000 through the air current pipe 2601. When the fuel is exhausted by the heating energy and a length thereof decreases, the fuel support 2647 may be pushed by an elastic force of the elastic member 2646 to cause the fuel 2648 to move toward the fuel module open surface 2656.

An absorbent member 2649 may be formed at the fuel module open surface 2656 or fuel in surface-contact with the fuel module open surface 2656. The absorbent member 2649 may include a material, which absorbs and stores fuel, or a material including a small aperture discharging a vapor and transmitting heating energy (light, beams, heat) or may have a cross shape to prevent the fuel 2648 from being led into the vaporization space 2629. The elastic member 2646 may be omitted, and adhesion or an internal vacuum force of the fuel support 2647, the fuel 2648, and the absorbent member 2649 of the fuel module 2643 may be used instead.

In the above-described exemplary embodiment without the elastic member 2646, the fuel 2648 in the fuel module 2643 may remain in contact with the absorbent member 2649 due to attraction generated while heating energy generated by the heating member 2625 vaporizes the fuel 2648 stored in the absorbent member 2649 or the fuel 2648 transmitted through the absorbent member 2649 in the vaporization space 2629. Since the fuel 2648 and the fuel support 2647 also remain in a contact state due to a vacuum force (or adhesion or attraction) inside the fuel module 2643, the fuel support 2647 may push the fuel 2648 toward the absorbent member 2649 (or the absorbent member may pull the fuel, and the fuel may pull the fuel support) as much as a volume of fuel consumed by vaporization such that the fuel 2648 and the absorbent member 2649 to continuously remain in a contact state. In the above-described configuration, to allow the fuel support 2647 to move in contact, an air current path (not shown) may be formed to suction outside air in a space in which the elastic member 2646 is omitted.

Figure 31:
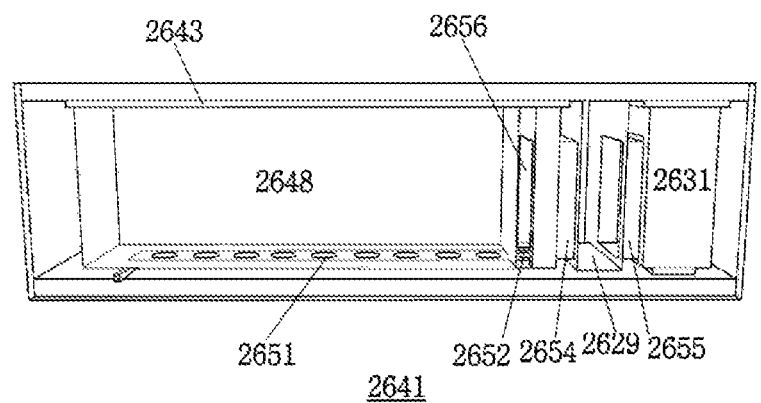
FIG. 31 is an internal view illustrating another configuration of the vaporization module according to the sixth exemplary embodiment of the present invention.

In addition, as shown in FIG. 31, when the fuel 2648 is attached or fixed to an inner surface of the fuel module 2643, a plurality of air current apertures may be formed in a part of the inner surface of the fuel module 2643 to allow outside air to flow therein. When the fuel 2648 is not exhausted and has a long length, a generated vapor may be led into the vaporization space 2629 through an air current aperture b 2652 in the inner surface. When the fuel 2648 is exhausted and has a length decreased as much as a position of an air current aperture a 2651, a vapor may be led into the vaporization space 2629 due to outside air which flows in through the air current aperture a 2651. The above-described configuration of a plurality of air current apertures may be applied to a case in which a length of fuel does not change according to use or to a case in which fuel such as herb leaves includes an air current path formed therein.

Figure 32A:
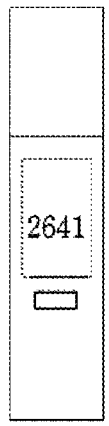
FIGS. 32A and 32B are yet another configuration diagram illustrating the vaporization module according to the sixth exemplary embodiment of the present invention.

In addition, although the vaporization module 2641 is formed such that a longitudinal direction of the body portion housing is perpendicularly coupled with a longitudinal direction of the vaporization module in FIGS. 28 and 29, parallel coupling may also be adopted by changing positions of an electric terminal, an air current aperture, and an air current pipe (refer to FIG. 32A). A plurality of such fuel modules 2643 coupled with or separated from the vaporization module 2641 may be formed. A fuel inlet may be additionally formed in the fuel module 2643 to fill fuel. To allow a user to recognize when to replace the fuel module 2643, a particular incense may be included in an end of the fuel 2648. The fifth and sixth exemplary embodiments may be provided in combination (for example, a fuel support and an absorbent member, which are combined with an elastic member, and a plurality of air current apertures in a fuel module).

In addition, in the above fifth and sixth exemplary embodiments, a vaporization module may be omitted and each of an absorbent member module (fuel module) and a heating module may be separately coupled with or separated from a module chamber open to both sides of a housing as shown in the first to fourth exemplary embodiments above. An absorbent member module (fuel module) or a heating module may be attached to a vaporization module without being separated from each other, and the vaporization module may be coupled with or separated from the module chamber open to both sides of the housing. In the sixth exemplary embodiment (including the first, second, third, and fourth exemplary embodiments), fuel may include a mesh support therein or a fuel storage space of a fuel module may include a plurality of inner partition walls similar to honeycombs to prevent leaning of fuel due to consumption during use.

Figure 32B:
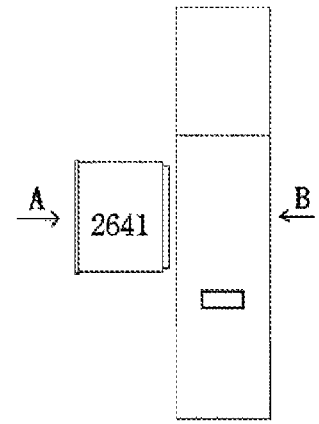

The following should be noted when the above-described first to sixth exemplary embodiments are implemented. A shape of a vaporizer is not limited to a quadrangular shape but may also include a cylindrical shape, a triangular shape, and the like based on a shape of a housing to couple or separate a module. Some surfaces of the module may protrude outward from a module chamber. A design of a structure in which one surface or both surfaces of a body portion housing are open may include front and rear surfaces of the housing having relatively long lengths or large areas and also side surfaces of the housing having relatively short lengths or small areas. For example, in the case of the sixth exemplary embodiment, as shown in FIG. 32B, the vaporization module may be coupled in a direction of an arrow A and separated in a direction of an arrow B through the side surfaces of the housing.

Figure 35:
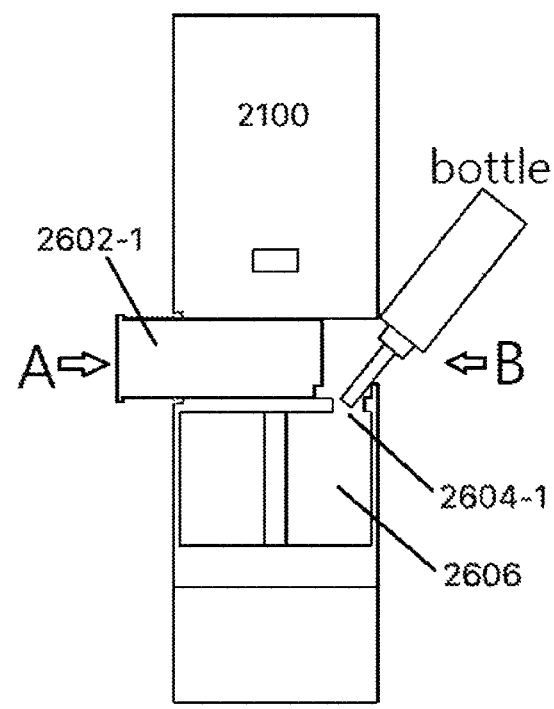
FIG. 35 illustrates a fuel injection use of a vaporization module coupled to the side of the body portion housing according to the present invention.

Likewise, referring to FIG. 35, the side coupling in the fifth exemplary embodiment, in which the fuel storage space and the vaporization module are included in the body portion, the vaporization module 2602-1 may be pushed and coupled in the direction of the side A of the body portion 2100, and the vaporization module 2602-1 may be pushed out in the direction of the side B. In addition, the vaporization module may be pushed to expose a fuel transport aperture 2604-1 to inject the fuel into the fuel storage space 2606 more easily.

In addition, as an example of the side surface being open, in the case of the fifth exemplary embodiment (refer to FIG. 20), one side surface may be open in a push-out module coupling-separation manner or three surfaces (front surface, rear surface, and side surface) of the body portion housing into which a module is inserted may be open to be coupled through the side surface. In particular, a separation method may include pulling the vaporization module toward the open side surface using the open front and rear surfaces. In the configurations of the fifth and sixth exemplary embodiments (refer to FIGS. 18 and 28), the vaporization modules 2602 and 2641 may not be separately formed and an absorbent member module (or a fuel module) or a heating module may be coupled or separated through open both sides of the body portion housing in a drawer manner.

In coupling between a module and a module chamber, sealing or waterproof coupling may refer to a state without outflows of a liquid and also a gas, light, beams, and heat. The coupling of the module may be firmly fixed by including one or more magnets or using an elastic fixing member or a fixing clip in the module chamber. In order to prevent a liquid and a gas from being discharged outward, uneven (protruding and depression) type coupling or combination of a convex line and a concave line may be included. A power module and a battery cell may also be waterproof-coupled and separated in a drawer manner by forming a power module chamber and a battery cell module chamber in the body portion housing such that a variety of power modules such as click type, electronic type, fingerprint-sensing type power modules, and the like, and a variety of types of battery cells having different capacities may be selectively replaced and applied.

The vaporization module may have a structure in which not both of the absorbent member module (or fuel module) and the heating module are coupled with or separated from the vaporization module. Instead, the vaporization module may be configured to couple or separate only the absorbent member module (or fuel module) or only the heating module.

The fuel module may store fuel in a hollow therein and may include one open surface, a light (beam)-transmitting member (half mirror) on one open surface, or an absorbent member on one open surface. An edge of a heating member, a heating module, or a vaporization module may include a heat dissipation material (heat dissipation plate). The heat dissipation material may include a multiple structure. In the case of the multiple structure, an inner structure includes a material having a high heat conductivity (for example, a graphene sheet, a graphite sheet, or the like) to protect the heating member by dissipating internal heat.

The heating member may include a (lamp) member that generates light energy such as laser, infrared rays, ultraviolet rays, a halogen lamp, and the like, or a member that generates microwaves, a heating wire (pipe), or the like. When the heating member includes the heating wire (pipe), the heating module may include a dense spirally circular or zigzag mesh on a particular surface thereof or may include a heating wire printed board. In particular, the heating member and the absorbent member may be disposed close to each other or come into surface contact with each other. Since the above-described configuration may have fuel between a surface of the absorbent member and a surface of the heating member, the heating wire may be prevented from being exposed to the air such that carbonization and/or generating of a harmful gas may be suppressed. In addition, the heating wire (pipe) may be fixed using the heating module. Heat may be supplied to the heating wire (pipe) in proximity to the absorbent member. Unlike a conventional method, since it is unnecessary to wind a heating wire (pipe) on glass fiber, manufacturing may become more efficient. The heating member including the heating wire (or including a case in which the heating wire is wound on the absorbent member) may be modularized to be sealed and (waterproof)-coupled or separated outside the housing in a drawer manner. Accordingly, the configuration of the heating wire (pipe) will be included in the present invention. When the heating wire (pipe) is in proximity to or comes into surface-contact with fuel (or the absorbent member), an inside of the vaporization module may be formed in an order of the absorbent member, the heating member, and a vaporization space.

The absorbent member (or fuel) may have a color (for example, black) sensitive to light (beam) based on a heating energy property of the heating member. A light reception panel 2679 (refer to FIG. 9) may be inserted into the absorbent member to effectively receive light energy. The light reception panel may have a heat-resistant material and may receive and convert light energy that passes through the absorbent member into vaporization (heat) energy (since the light energy of the heating member uniformly heats an entire surface of the light reception panel, there is a difference with a conventional heating wire vaporization method in the related art). Alternatively, the light reception panel may reflect the received light energy to secondarily irradiate the absorbent member which has been firstly irradiated (double heating). The light reception panel may include a plurality of drilled apertures in a surface thereof to allow fuel to freely move through the absorbent member. A plurality of such light reception panels may be included.

A method of emitting heating (light) energy may include a continuous wave (CW) of continuously emitting heating (light) energy while a power button is pushed and a pulse wave (PW) (or a discrete wave) of emitting heating (light) energy at particular intervals like pulses. A circuit controlling the same may be built in the heating module or the power module. The method may be selected by a selection button provided outside the housing. For example, when the PW is applied and a main component of a raw material to be vaporized by heating (light) energy is a mixed solution of propylene glycol and vegetable glycerin, since vaporization temperatures of propylene glycol and vegetable glycerin are 190 and 290 degrees Celsius, respectively, and ignition temperatures of propylene glycol and vegetable glycerin are 420 and 390 degrees Celsius, respectively, the PW may be applied to maintain a temperature of heating (light) energy within a range of 190 to 390 degrees Celsius, and to avoid approaching the ignition temperatures. Accordingly, an internal circuit may be configured to allow temperature data and pulses to work along with each other so as to retard (e.g., slow down) pulses such that a temperature of the heating (light) energy is prevented from increasing when the temperature approaches 390 degrees Celsius. A selection button including a control circuit designed to select a level or wavelength of light energy based on applied fuel may be included.

Figure 30:
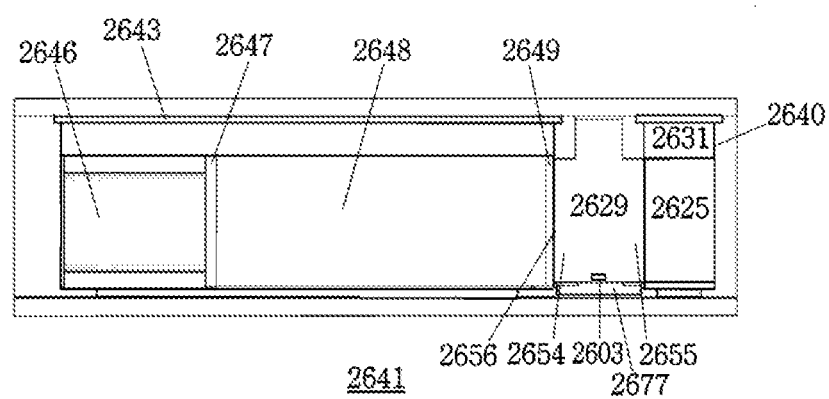
FIG. 30 is a cross-sectional view illustrating a configuration of the vaporization module according to the sixth exemplary embodiment of the present invention.

As shown in FIGS. 8, 23, and 30, a water storage space 2677, into which a member absorbing and storing water is inserted, may be formed to absorb and store a residual vapor which flows down from the air current pipe 2003 of the suction portion 2000, the air current pipes 2103 and 2601 of the fuel chamber 2607, or the vaporization spaces 2106 and 2629. The water storage space 2677 may be formed as a water storage module chamber, and a water storage module which accommodates the member absorbing and storing water may be formed. Both sides of the module or the housing of the body portion may be open to be sealed (waterproof)-coupled or separated by pushing or pulling the module in a drawer manner (with protrusion and depression coupling portion or a structure of a waterproof convex line and a waterproof concave line). When water is absorbed and stored in the water storage module, a waterlogging phenomenon or a humidification phenomenon which occurs due to a backflow of a vapor, which remains in a suction portion of a conventional vaporizer or an air current pipe of a cartridge, into a vaporizing device may be prevented.

In addition, according to the configuration of coupling and separation of the housing having both open sides which is an aspect of the present invention, a circuit board may be coupled with and separated from the module or the housing in the drawer manner such that the circuit board having a variety of functions may be replaced more easily as necessary. For example, in the heating module separated from the vaporization module of the fifth exemplary embodiment in the drawer manner, a circuit board module chamber open to both sides of a heating module housing may be formed such that circuit boards having different functions may be inserted as necessary or a circuit board may be inserted in a connection part housing of a battery cell and the heating module. For reference, as an example of different functions of circuit boards, a heating temperature range may be differently limited, a function of working along with a smart phone (Bluetooth) may be included, a guide voice for blind people may be included, and/or a global positioning system (GPS) may be included.

In the present invention, shapes of the vaporizer 2500, modules, and module chambers are not limited to a quadrangular shape. A coupling manner between components may include various manners such as thread, magnetic manners, and the like. A fuel module chamber, a heating module chamber, an absorbent member module chamber, and the like may be configured in a push-out button type in which a housing includes an open surface and the fuel module, the heating module, the absorbent member module, and the like are coupled and fixed by being pushed once and are separated and discharged by being pushed again. To prevent a module from being discharged by inadvertent pushing or to protect the module, a protection cover may be included in the housing. A waterproof member, a closing member, a heating energy reflecting member, and the like, which prevent an outflow of a liquid, a gas, or heating energy (light, beams, and heat) in coupling between components or coupling between a module and a housing may be additionally included.

In order to prevent light leakage to the suction portion, utilizing the characteristics of vapor and air moving in a curved line, and light moving in a straight line, the suction portion, the air current pipe, or the vaporization space described in the above exemplary embodiments may be divided into a plurality of vertical or horizontal partitions, or a light reflection structure may be included in a portion where vapor moves to obstruct light and to discharge only vapor to the suction portion. The frame of the vaporizing space may also be configured to be inserted and separated into a body portion housing or a vaporizing module.

A solid fuel (or a jelly type fuel) may be coupled with or filled in a fuel chamber without using a fuel module. In addition, to improve safety of a user, a material of a component may include tempered glass having a function of canceling a wavelength of applied heating energy. To restrict heating energy to be safely used only for vaporization of the present invention, functional (convex, concave, and the like) lenses may be prevented from being separated from a heating member when the module is manufactured such that when heating energy deviates from a vaporizing focal point, a wavelength may be gradually extended or reduced to become weak or to dissipate. An electric terminal circuit may be formed to apply power to the heating module when the fuel module is coupled with the housing. Alternatively, a sensor may be attached to the heating module or an inside of the housing such that heating energy may be emitted when an object is recognized within a particular distance (focal length).

Furthermore, types of heating elements (e.g., light emitting diodes (LED)) and ranges of wavelength, vibration, frequency, and the like of heating energy are not limited. In the above exemplary embodiments, examples of the heating element may include various light emitting devices that emit light energy from a semiconductor structure, such as LEDs similar in structure to laser, as well as light emitting devices such as laser, infrared, ultraviolet, and halogen lamp. The light emitting element may also be formed in the form of dots, lines, surfaces, or a mixture thereof, and a mixture of various light emitting elements.

The air flow passage may be configured to pass around the heating member to flow the air entering from the outside or the vapor discharging from the vaporization space for cooling the heating member. Furthermore, due to the competition, reflection and superposition of light energy, a heating member driven by low temperature and low power may be applied.

When the magnet is configured for coupling of the module to the module chamber, a repulsive magnetic force may also be used in addition to the attractive magnetic force. The module and the module chamber may be configured to prevent the inflow of outside substances and to prevent the internal vapor flowing out to the outside due to the watertight coupling by the stepped edges or concave convex line.

A variety of modifications may be made without departing from the spirit of the present invention, the configuration described in one exemplary embodiment may also be applied to other exemplary embodiments similarly or in a modified manner, and the scope of the present invention is not limited to the above-described exemplary embodiments and should be determined by the following claims and equivalents thereof.

What is claimed is:

1. A modularized vaporizer comprising a suction portion and a body portion, wherein the body portion comprises:
   a body portion housing;
   a fuel module that stores a fuel and includes an open surface to receive a light energy;
   a heating module coupled to the body portion housing and disposed apart from the fuel module, wherein the heating module includes a heating member that emits the light energy;
   a circuit that controls the heating module by adjusting the light energy to be emitted in a continuous wave or a pulse wave to cause the fuel to be maintained between a vaporization temperature and an ignition temperature thereof;
   a vaporization space disposed between the heating module and the fuel module, wherein a vapor is released into the vaporization space by the light energy emitted from the heating module toward the fuel module through the vaporization space; and
   an air current pipe which is a path for transferring the vapor released in the vaporization space to the suction portion,
   wherein the body portion housing includes at least one module chamber to accommodate the fuel module or the heating module, and each of the at least one module chamber includes a first open surface and a second open surface across the body portion housing, and
   wherein the fuel module or the heating module is pushed into the first open surface of the module chamber to be coupled therewith, and is pushed from the second open surface of the module chamber to be separated therefrom.

2. The modularized vaporizer of claim 1, wherein the suction portion and the body portion are configured to be separated from each other,
- wherein a fuel module chamber is formed within the body portion housing and configured to receive the fuel module when the suction portion is separated from the body portion, and
- wherein an open surface is provided at one side of the fuel module chamber to receive the light energy.

3. The modularized vaporizer of claim 1, wherein the heating member includes a light emitting diode.

4. The modularized vaporizer of claim 1, wherein the body portion comprises a module chamber that accommodates an absorbent member module in which the fuel is absorbed.

5. The modularized vaporizer of claim 1, wherein an inlet is formed in one surface of the fuel module,
- wherein an inlet stopper is formed on a surface of the module chamber that accommodates the fuel module, and
- wherein the inlet stopper is configured to close the inlet of the fuel module when the fuel module is coupled to the module chamber that accommodates the fuel module.

6. The modularized vaporizer of claim 1, wherein each of the at least one module chamber comprises one or more magnets.

7. The modularized vaporizer of claim 1, wherein the open surface of the fuel module, which receives the light energy, comprises a light transmitting member that discharges the vapor, or an absorbent member, and
- wherein the fuel module includes a fuel support and an elastic member that is coupled to the fuel support, and the fuel support is configured to push the fuel toward the open surface of the fuel module.

8. The modularized vaporizer of claim 1, wherein the fuel module includes a fuel support, which abuts the fuel and an inner sidewall of the fuel module,
- wherein an absorbent member is provided in the open surface of the fuel module or the fuel in contact with the open surface of the fuel module, and
- wherein the fuel in the fuel module comes into contact with the absorbent member as the fuel is vaporized due to attraction generated while the fuel is vaporized through the absorbent member by the light energy emitted toward the absorbent member and a pressure inside the fuel module, and the fuel support in contact with the fuel is pulled by the fuel toward the absorbent member while maintaining a contact with the fuel.

9. The modularized vaporizer of claim 1, further comprising:
- a control button disposed in the body portion housing.

10. The modularized vaporizer of claim 1, wherein the heating module comprises a plurality of light energy generation portions,
- wherein the light energy generation portions are formed to face the fuel at a slant angle, or light energy generated by some of the light energy generation portions reaches the fuel via a reflector, and
- wherein a plurality of light energies are emitted toward a particular part of the fuel.

11. The modularized vaporizer of claim 4, wherein the absorbent member module comprises:
- a fuel transfer aperture through which the fuel of the fuel module moves to an absorbent member;
- an external air current aperture through which outside air flows in; and
- an internal air current aperture through which the air flowing in through the external air current aperture flows out to the absorbent member,
- wherein the internal air current aperture is blocked from the fuel module and the fuel transfer aperture, and the absorbent member is inserted into an open surface of the internal air current aperture, and
- wherein the fuel of the fuel module or the fuel transfer aperture continuously flows into the absorbent member due to a flowing force of the air flowing in through the external air current aperture that passes the absorbent member through the internal air current aperture due to a suction force of the suction portion and being discharged into the vaporization space.

12. The modularized vaporizer of claim 4, wherein the fuel module or the absorbent member module comprises a light reflecting plate to allow the light energy generated by the heating module to pass through an absorbent member or the fuel and to be subsequently reflected by the light reflecting plate and emitted toward the absorbent member or the fuel.

* * * * *